(12) United States Patent
Chen et al.

(10) Patent No.: US 8,076,482 B2
(45) Date of Patent: *Dec. 13, 2011

(54) 3,3'-SPIROINDOLINONE DERIVATIVES

(75) Inventors: Li Chen, Shanghai (CN); Xingchun Han, Shanghai (CN); Song Yang, Shanghai (CN); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,687

(22) Filed: Mar. 29, 2010

(65) Prior Publication Data

US 2010/0273819 A1    Oct. 28, 2010

Related U.S. Application Data

(60) Provisional application No. 61/171,970, filed on Apr. 23, 2009.

(51) Int. Cl.
*A61K 31/438* (2006.01)
*C07D 401/04* (2006.01)

(52) U.S. Cl. .......... 546/18; 514/278
(58) Field of Classification Search .......... 546/18; 514/278

See application file for complete search history.

(56) References Cited

U.S. PATENT DOCUMENTS

| 7,495,007 | B2 | 2/2009 | Chen et al. | |
|---|---|---|---|---|
| 7,553,833 | B2 | 6/2009 | Liu et al. | |
| 7,638,548 | B2 | 12/2009 | Liu et al. | |
| 7,776,875 | B2 * | 8/2010 | Chen et al. | 514/278 |
| 2007/0213341 | A1 | 9/2007 | Chen et al. | |
| 2008/0009486 | A1 | 1/2008 | Chen et al. | |
| 2008/0114013 | A1 | 5/2008 | Liu et al. | |

FOREIGN PATENT DOCUMENTS

| EP | 0288847 | 4/1988 |
|---|---|---|
| EP | 0 947 511 A1 | 10/1999 |
| WO | 01/05790 | 1/2001 |
| WO | 2006091646 | 8/2006 |
| WO | 2007104664 | 9/2007 |
| WO | 2007104714 | 9/2007 |
| WO | 2008080822 | 7/2008 |
| WO | 2008005268 | 10/2008 |
| WO | 2009080488 | 7/2009 |

OTHER PUBLICATIONS

Hans-Dieter Arndt, Dr. Kleine Molekule pp. 4664-4673—XP-002465843.
J. Amer. Chem. Soc. (2005) 127 p. 10130.
Howard C. Ansel, Pharmaceutical Dosage Forms and Drug Delivery Systems, 6th Ed. 1995, pp. 196, 456-457.
Ghosez, L., etal Tetrahedron 1995—11021-11042.
Lippa, B. et al Bioorganic & Med. Chem. Letters, 18 (11), 2008—3359-3363.
Ding et al, J. Med. Chem. (2006) 49:3432-3435.
Sairam, P., Elsevier 303-306.
Simplicio,A., Molecular Diversity Preservation International, 519-547—XP-002503564.

* cited by examiner

*Primary Examiner* — Rita Desai
(74) *Attorney, Agent, or Firm* — George W. Johnston; Patricia S. Roca-Tramaloni

(57) ABSTRACT

There are provided compounds of the formula

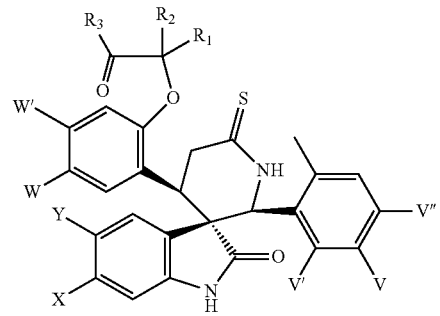

or a pharmaceutically acceptable salt or ester thereof wherein X, Y, W, W', V, V', V'', $R_1$, $R_2$ and $R_3$ are as herein described. The compounds have utility as antiproliferative agents, especially, as anticancer agents.

4 Claims, No Drawings

3,3'-SPIROINDOLINONE DERIVATIVES

PRIORITY TO RELATED APPLICATION(S)

This application claims the benefit of U.S. Provisional Application No. 61/171,970 filed Apr. 23, 2009, which is hereby incorporated by reference in its entirety.

SUMMARY OF THE INVENTION

The present invention relates to analogues of spiroindolinones having the formula

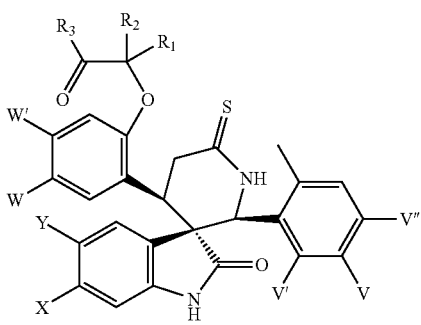

or a pharmaceutically acceptable salt or ester or enantiomers thereof wherein X, Y, W, W', V, V', V", $R_1$, $R_2$ and $R_3$ are as herein described. The compounds have utility as antiproliferative agents, especially, as anticancer agents.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am. Chem. Soc., 2005, 127, 10130 and also in US-2007-0213341-A1 published Sep. 13, 2007.

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

DETAILED DESCRIPTION OF THE INVENTION

The present invention relates to spiroindolinones of the formula

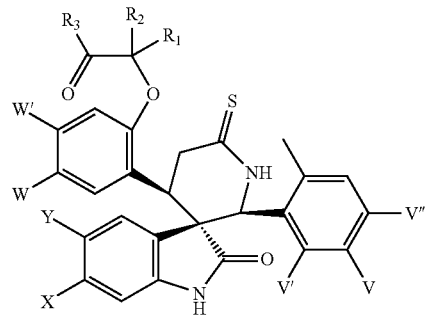

wherein
X is Cl, F or Br,
Y is hydrogen or F,
V is F or Cl,
V' is hydrogen or F,
V" is hydrogen or F,
W is F, Cl or Br,
W' is hydrogen or F,
$R_1$ and $R_2$ are hydrogen, methyl, ethyl or propyl,
or $R_1$ and $R_2$ may link to form a cyclic structure selected from a substituted or unsubstituted cycloalkyl.
$R_3$ is selected from OH, OR', $NH_2$, NHR', NR'R", NHOR' or NHS($=$O)$_2$R",
R', R" is selected independently from the group consisting of lower alkyl, substituted alkyl, cycloalkyl and substituted cycloalkyl
and the pharmaceutically acceptable salts and esters and enantiomers thereof.

Preferred are compounds of formula I wherein X is Cl, Y is hydrogen, V is F or Cl, V' is hydrogen, V" is hydrogen, W is Cl, W' is hydrogen, $R_1$, $R_2$ are methyl or ethyl and $R_3$ is OH or NHS($=$O)$_2$Me.

Most preferred compounds are those of the formula:

chiral (2'S, 3S, 4'R)-6-chloro-4'-[5-chloro-2-(1-hydroxycarbonyl-1-methyl-ethoxy)-phenyl]-2'-(5-fluoro-2-methyl-phenyl)-6'-thioxo spiro[3H-indole-3,3'-piperidine]-2(1H)-one, racemic (2'S, 3S, 4'R)-6-chloro-4'-[5-chloro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one, chiral (2'S, 3S, 4'R)-6-chloro-4'-[5-chloro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one, chiral (2'S, 3S, 4'R)-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one, chiral (2'R, 3R, 4'S)-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one, chiral (2'S, 3S, 4'R)-6-chloro-4'-[5-chloro-2-(2-methanesulfonylamino-1,1-diethyl-2-oxo-ethoxy)-phenyl]-2'-(5-chloro-2-methyl-phenyl)-6'-thioxo spiro[3H-indole-3,3'-piperidine]-2(1H)-one, racemic (2'S, 3S, 4'R)-6-chloro-4'-[5-chloro-2-(1-ethoxycarbonyl-1-propyl-butoxy)-phenyl]-2'-(5-fluoro-2-methyl-phenyl)-6'-thioxo spiro[3H-indole-3,3'-piperidine]-2(1H)-one, chiral (2'S, 3S, 4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-6'-thioxo spiro[3H-indole-3,3'-piperidine]-2(1H)-one, racemic (2'S, 3S, 4'R)-6-chloro-4'-[5-chloro-2-(1-methoxycarbonyl-cyclobutoxy)-phenyl]-2'-(5-fluoro-2-methyl-phenyl)-6'-thioxo spiro[3H-indole-3,3'-piperidine]-2(1H)-one, racemic (2'S, 3S, 4'R)-6-chloro-4'-[5-chloro-2-(2-methoxycarbonyl-methoxy)-phenyl]-2'-[5-difluoro-2-methyl-phenyl]-6'-thioxo spiro[3H-indole-3,3'-piperidine]-2(1H)-one, racemic (2'S, 3S, 4'R)-6-chloro-4'-[5-chloro-2-(1-methoxycarbonyl-1-methyl-ethoxy)-phenyl]-2'-(4,5-difluoro-2-methyl-phenyl)-6'-thioxo spiro[3H-indole-3,3'-piperidine]-2(1H)-one, racemic (2'R, 3R, 4'S)-6-chloro-4'-[5-chloro-4-fluoro-2-methoxy-phenyl]-2'-(5-fluoro-2-methyl-phenyl)-6'-thioxo spiro[3H-indole-3,3'-piperidine]-2(1H)-one, racemic (2'S, 3S, 4'R)-6-chloro-4'-[5-chloro-2-(1-methoxycarbonyl-1-methyl-ethoxy)-phenyl]-2'-(5,6-difluoro-2-methyl-phenyl)-6'-thioxo spiro[3H-indole-3,3'-piperidine]-2(1H)-one, racemic (2'S, 3S, 4'R)-6-chloro-4'-[5-chloro-4-fluoro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one, racemic (2'S, 3S, 4'R)-6-chloro-4'-[5-chloro-2-(1-methoxycarbamoyl-1-methyl-ethoxy)-phenyl]-2'-(5-fluoro-2-methyl-phenyl)-6'-thioxo spiro[3H-indole-3,3'-piperidine]-2(1H)-one and racemic (2'S, 3S, 4'R)-6-chloro-4'-[5-chloro-2-(1-methoxycarbamoyl-1-ethyl-propoxy)-phenyl]-2'-(5-fluoro-2-methyl-phenyl)-6'-thioxo spiro[3H-indole-3,3'-piperidine]-2(1H)-one.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 456-457.

The compounds of formula I as well as their salts have at least one asymmetric carbon atom and therefore may be present as racemic mixtures or different stereoisomers. The various isomers can be isolated by known separation methods, e.g., chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compound of formula I and are cleaved in vivo (in the organism) to the corresponding active carboxylic acid or alcohol respectively.

SYNTHESIS

Compounds of this invention in formula I or II can be synthesized according to the following general schemes. It will be readily apparent to those of ordinary skill in the art that compounds of formula I can be prepared by substitution of the reagents or agents in the general synthesis routes. The starting materials are either commercially available or can be synthesized by well-established literature methods known to those of ordinary skill in the art. Using purification by chiral chromatography, compounds in formula II can be obtained as an optically pure or enriched enantiomers.

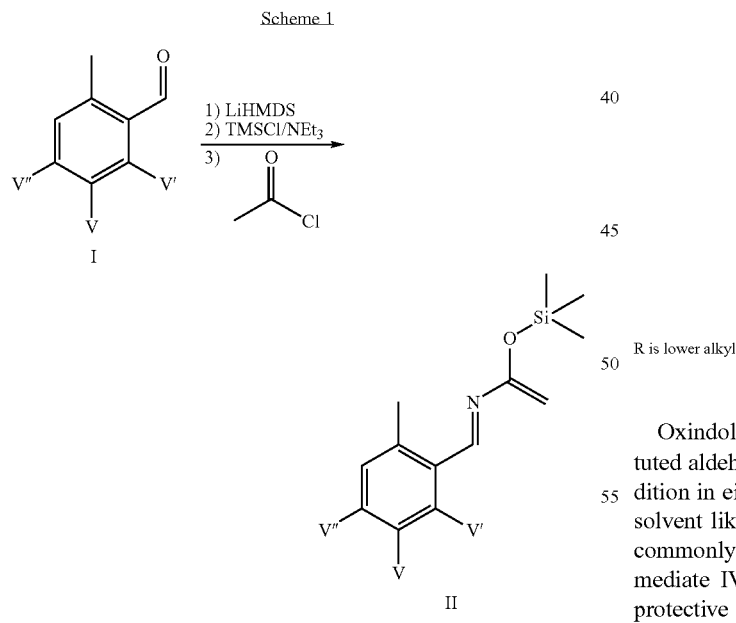

In general an appropriately selected aldehyde I can be reacted with lithium hexamethyldisilamide, chlorotrialkylsilane and acetyl chloride in a one-pot, multi-steps manner to generate 2-aza-1,3-butadiene II (Scheme I) and can be used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited therein). The appropriately selected aldehyde I are either commercially available or can be synthesized by well-established multiple literature methods.

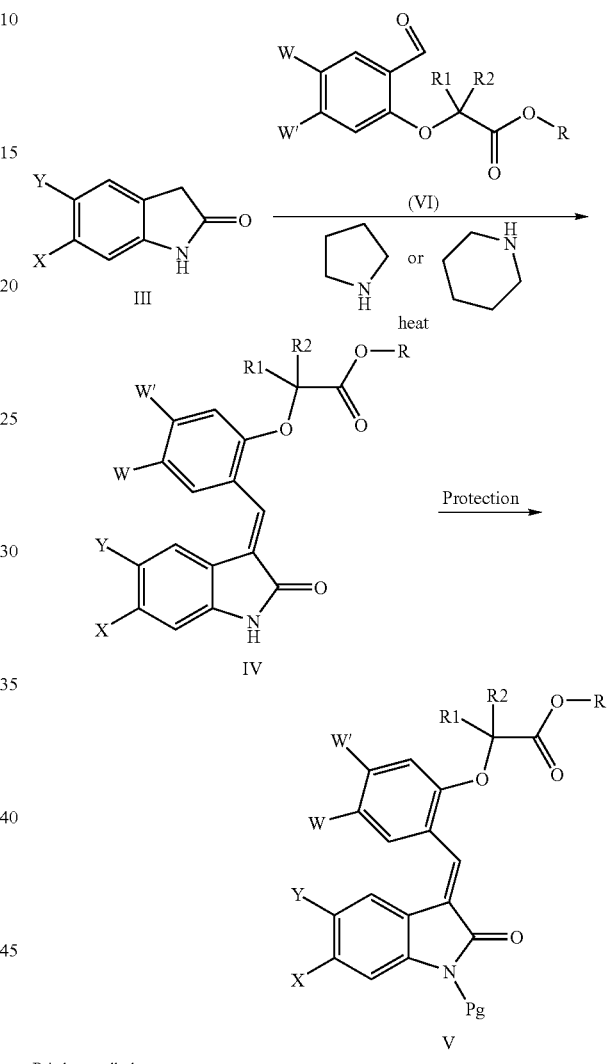

R is lower alkyl

Oxindole III can be reacted with an appropriately substituted aldehyde VI in the presence of base under heated condition in either a protic like methanol, ethanol or an aprotic solvent like toluene, o-xylene to give intermediate IV. The commonly used base is either pyrrolidine or piperidine. Intermediate IV can be protected to give intermediate V. The protective group can be attached by using ethyl chloroformate, di-tert-butyl dicarbonate, SEM-Cl, benzyl bromide, and a base like 4-(dimethylamine)pyridine (DMAP), triethylamine, NaH, or LiH according to well established literature procedures. Examples of protective group formation and their deprotection have been described and reviewed comprehensively by Greene, T. W. et al in "Protective Groups in Organic Synthesis, $2^{nd}$ Edition. John Wiley & Sons Inc.

Scheme 3

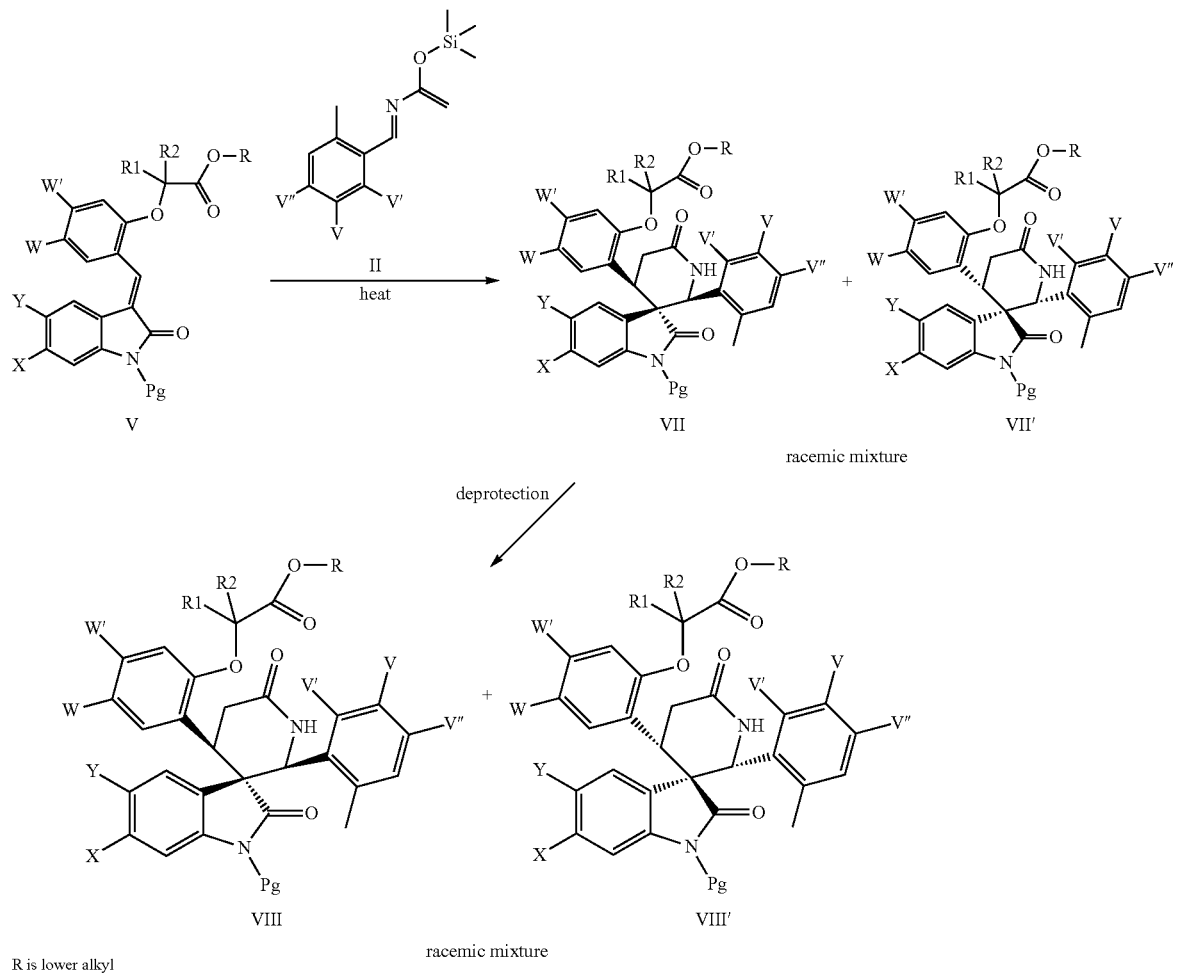

R is lower alkyl

Intermediate V can be reacted with a selected 2-aza-butadiene II prepared in Scheme 1 in toluene or o-xylene under heating from 110° C. to 160° C. and anhydrous condition to form intermediate VII and VII' as the major products shown as a racemic mixture of two enantiomers. A subsequent reaction to remove protective group (Pg) leads to various $R_1$, $R_2$ derivatized compound VIII and VIII'. (Scheme 3). In the case Pg is Boc group, Boc group can be removed by either trifluoroacetic acid or prolonged heating at a temperature between 110 to 116° C. during aza Diels-Alder reaction between V and II. Racemic mixture of VII and VII' or VIII and VIII' can be readily resolved into two chiral enantiomers by chiral Super Fluid Chromatography (SFC) or chiral HPLC or chiral column chromatography.

Scheme 4

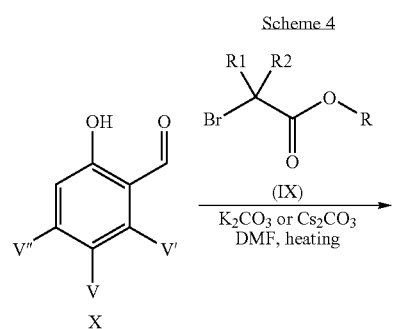

-continued

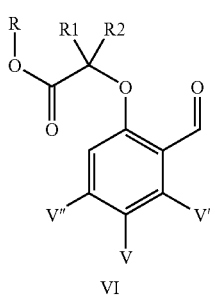

When R1, R2 are both methyl or linked to form a cycloalkyl group, intermediate VI in Scheme 2 can be prepared by treatment of substituted benzaldehyde X, and a readily available reagent IX, a base like $K_2CO_3$ or $Cs_2CO_3$ in anhydrous N,N-dimethylformamide under heating conditions. (Scheme 4). When R1 or R2 is ethyl or n-propyl, intermediate VI in Scheme 2 can be prepared in a synthetic route illustrated in Scheme 5. The aldehyde X is either commercially available or readily accessible from literature procedures.

Scheme 5

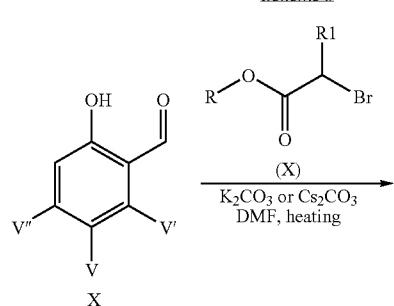

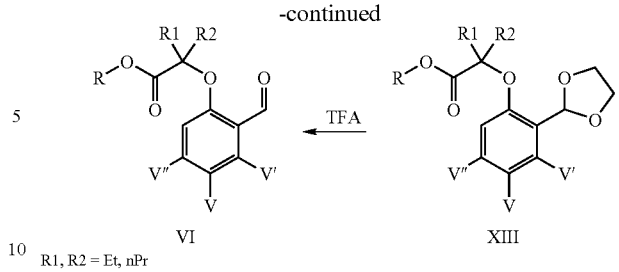

R1, R2 = Et, nPr

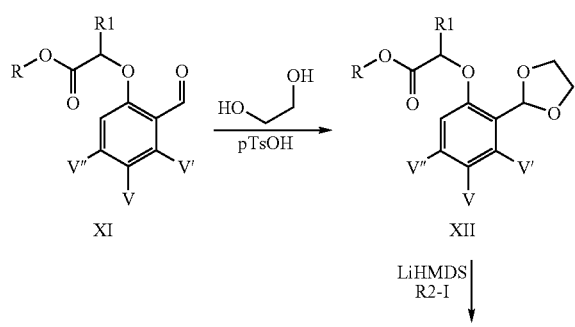

Compound VIII is hydrolyzed to acid XIV, followed by a coupling reaction using well-known methods to afford sulfonylamide analogues XV. Compounds VIII, XIV, XV can be converted into their corresponding 6-thiocarbonyl analogues XIX, XVIII or XVI by treatment with either Lawesson's Reagent or $P_2S_5$ in aprotic solvents like toluene under heated or ambient temperature. Alternatively, acid XIV can be reacted with R'NH$_2$, R'R"NH, or R"ONH$_2$ using HATU or other well known coupling reagent and a base to afford its corresponding amide analogue, followed by treatment with either Lawesson's Reagent or $P_2S_5$ in aprotic solvents like toluene under heated or ambient temperature to give analogue XVII (Scheme 6). R, R', R" is independently selected from lower alkyl, substituted alkyl, cycloalkyl and substituted cycloalkyl Scheme 6

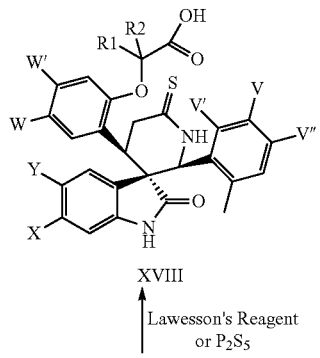

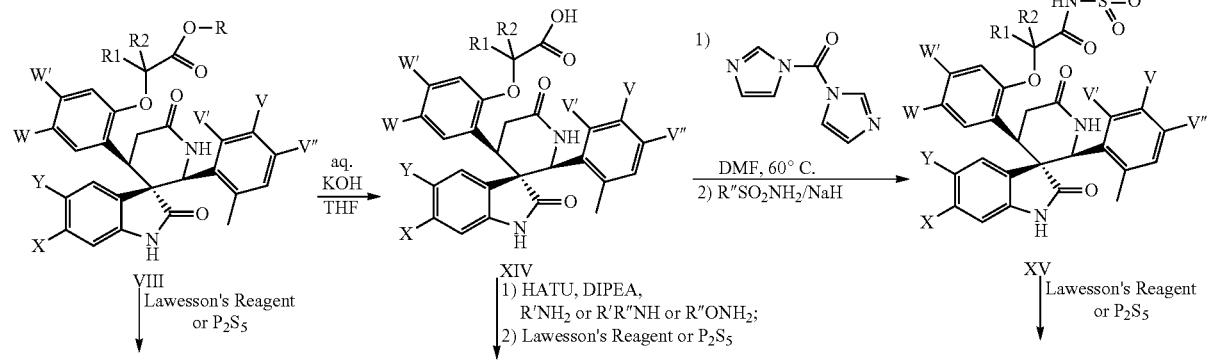

-continued

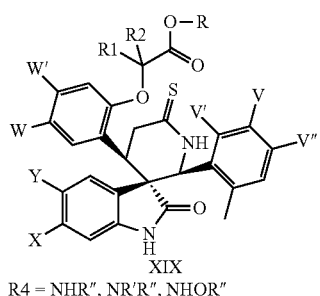
XIX
R4 = NHR'', NR'R'', NHOR''

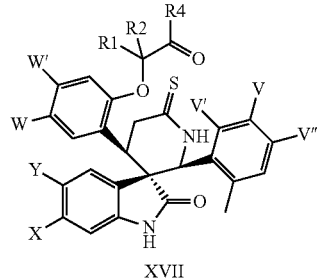
XVII

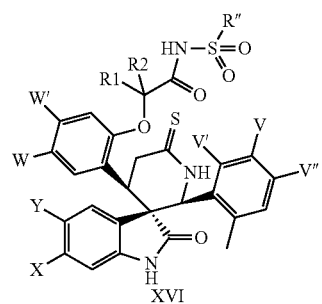
XVI

The following examples and references are provided to aid the understanding of the present invention, the true scope of which is set forth in the appended claims.

EXAMPLE 1

Preparation of intermediate 2-(4-chloro-2-formyl-phenoxy)-2-methyl-propionic acid methyl ester

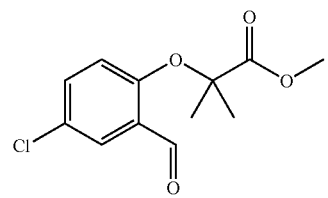

M.W. 256.05 $C_{12}H_{13}ClO_4$

A mixture of 5-chloro-2-hydroxy-benzaldehyde (7 g, 45 mmol), 2-bromo-2-methyl-propionic acid ethyl ester (10.4 g, 58 mmol), $K_2CO_3$ (18.6 g, 135 mmol) and KI (0.97 g, 5.8 mmol) in DMF (20 mL) was heated at 110° C. for 3 h. Then the mixture was filtered and the filtrate was concentrated. The residue was used into next step reaction without further purification (7 g).

EXAMPLE 2

Preparation of intermediate E/Z-2-[4-chloro-2-(6-chloro-2-oxo-1,2-dihydro-indol-3-ylidenemethyl)-phenoxy]-2-methyl-propionic acid methyl ester

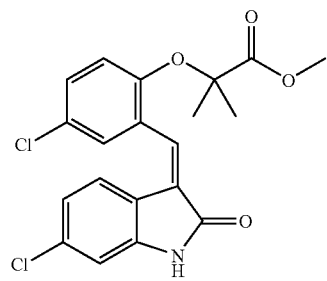

M.W. 406.27 $C_{20}H_{17}Cl_2NO_4$

To the mixture of 6-chloro-1,3-dihydro-indol-2-one (43 g, 0.26 mol) and 2-(4-chloro-2-formyl-phenoxy)-2-methyl-propionic acid methyl ester (66 g, 0.26 mol) in methanol (700 mL) was added pyrrolidine (22 g, 0.31 mol) dropwise. The mixture was then heated at 70° C. for 1 h. After cooled to room temperature, the mixture was filtered and resulting precipitate was collected, dried to give the title compound as a yellow solid (76 g).

EXAMPLE 3

Preparation of intermediate E/Z-6-chloro-3-[5-chloro-2-(1-methoxycarbonyl-1-methyl-ethoxy)-benzylidene]-2-oxo-2,3-dihydro-indole-1-carboxylic acid tert-butyl ester

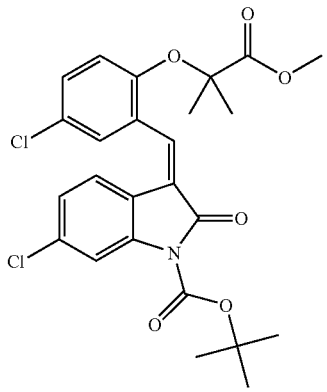

M.W. 520.41 $C_{26}H_{27}Cl_2NO_6$

At room temperature, to a solution of E/Z-2-[4-chloro-2-(6-chloro-2-oxo-1,2-dihydro-indol-3-ylidenemethyl)-phenoxy]-2-methyl-propionic acid methyl ester (73 g, 0.18 mol) in dichloromethane (700 mL) was added di-tert-butyl-dicarbonate (40 g, 0.18 mol), followed by the addition of 4-dimethylaminopyridine (4 g, 0.036 mol). The reaction mixture was stirred at room temperature for 1 h. Then the mixture was concentrated and the residue was purified by chromatography to give the title compound as an orange solid (86 g).

EXAMPLE 4

Preparation of intermediate 1-(5-fluoro-2-methyl-1phenyl)-3-trimethylsilyoxy-2-aza-1,3-butadiene

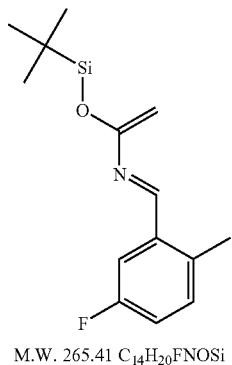

M.W. 265.41 C$_{14}$H$_{20}$FNOSi

To dry tetrahydrofuran (400 mL) was added 1M THF solution of LiHMDS (420 mmol, 420 mL) under argon at room temperature, followed by the addition of 5-fluoro-2-methyl-benzaldehyde (58 g, 420 mmol). After the mixture was stirred at room temperature for 1 h, trimethylsilyl chloride (53.2 mL, 420 mmol) was added dropwise. Then the temperature of the mixture was lowered to 0° C. on a cooling ice bath. To this mixture was added triethylamine (76 mL, 544 mmol) in one portion, followed by the dropwise addition of a solution of acetyl chloride (38.8 ml, 544 mmol) in diethyl ether (500 mL). The cooling bath was removed, and the mixture was stirred at room temperature overnight. The mixture was quickly filtered on celite under nitrogen, and filtrate was concentrated under reduced pressure to give crude 1-(5-fluoro-2-methylphenyl)-3-trimethylsilyoxy-2-aza-1,3-butadiene as a yellow gum and used for the next step without further purification.

EXAMPLE 5

Preparation of intermediate racemic (2'S, 3S, 4'R)-6-chloro-4'-[5-chloro-2-(1-methoxycarbonyl-1-methyl-ethoxy)-phenyl]-2'-(5-fluoro-2-methyl-phenyl) spiro [3H-indole-3,3'-piperidine]-2,6'(1H)-dione

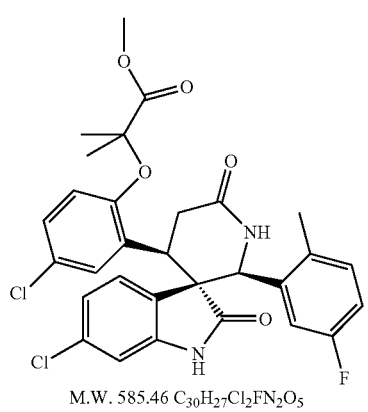

M.W. 585.46 C$_{30}$H$_{27}$Cl$_2$FN$_2$O$_5$

A mixture of E/Z-6-chloro-3-[5-chloro-2-(1-methoxycarbonyl-1-methyl-ethoxy)-benzylidene]-2-oxo-2,3-dihydro-indole-1-carboxylic acid tert-butyl ester (86 g, 166 mmol) and 1-(5-fluoro-2-methyl-1phenyl)-3-trimethylsilyoxy-2-aza-1,3-butadiene (248 mmol) in toluene (248 mL) was heated at 60° C. for 3 h, and concentrated in vacuo. To the residue was added DCM (300 mL) and TFA (50 mL), and the resulting solution was stirred at room temperature for 3 h, then concentrated in vacuo, partitioned between ethyl acetate and diluted aqueous NaOH solution. The organic layer was washed with water, dried over anhydrous Na$_2$SO$_4$, concentrated. The residue was purified by flash column chromatography to give the title compound as white solid (33 g).

EXAMPLE 6

Preparation of intermediate chiral (2'S, 3S, 4'R)-6-chloro-4'-[5-chloro-2-(1-methoxycarbonyl-1-methyl-ethoxy)-phenyl]-2'-(5-fluoro-2-methyl-phenyl) spiro [3H-indole-3,3'-piperidine]-2,6'(1H)-dione

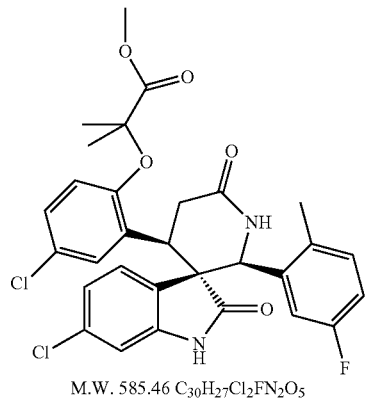

M.W. 585.46 C$_{30}$H$_{27}$Cl$_2$FN$_2$O$_5$

Separation of the two enantiomers from racemic (2'S, 3S, 4'R)-6-chloro-4'-[5-chloro-2-(1-methoxycarbonyl-1-methyl-ethoxy)-phenyl]-2'-(5-fluoro-2-methyl-phenyl) spiro [3H-indole-3,3'-piperidine]-2,6'(1H)-dione (14 g) was conducted by chiral SFC to provide chiral (2'S, 3S, 4'R)-6-chloro-4'-[5-chloro-2-(1-methoxycarbonyl-1-methyl-ethoxy)-phenyl]-2'-(5-fluoro-2-methyl-phenyl) spiro[3H-indole-3,3'-piperidine]-2,6'(1H)-dione as a white solid (4.8 g) and chiral (2'R, 3R, 4'S)-6-chloro-4'-[5-chloro-2-(1-methoxycarbonyl-1-methyl-ethoxy)-phenyl]-2'-(5-fluoro-2-methyl-phenyl) spiro[3H-indole-3,3'-piperidine]-2,6'(1H)-dione as a white solid (4.7 g).

EXAMPLE 7

Preparation of intermediate chiral (2'S, 3S, 4'R)-6-chloro-4'-[5-chloro-2-(1-hydroxycarbonyl-1-methyl-ethoxy)-phenyl]-2'-(5-fluoro-2-methyl-phenyl) spiro [3H-indole-3,3'-piperidine]2,6'(1H)-dione

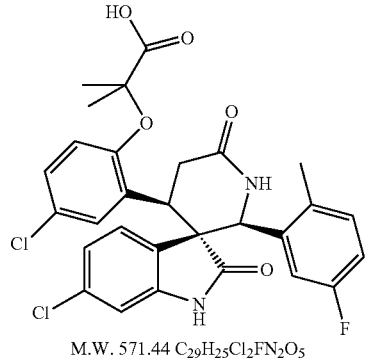

M.W. 571.44 C$_{29}$H$_{25}$Cl$_2$FN$_2$O$_5$

A mixture of chiral (2'S, 3S, 4'R)-6-chloro-4'-[5-chloro-2-(1-ethoxycarbonyl-1-methyl-ethoxy)-phenyl]-2'-(5-fluoro-2-methyl-phenyl) spiro[3H-indole-3,3'-piperidine]-2,6'(1H)-dione (4.8 g, 8.03 mmol), NaOH (1.6 g, 40 mmol), H₂O (30 mL) and methanol (50 mL) was heated at 80° C. for 1 h. Then methanol was removed under reduced pressure and the aqueous solution was acidified by concentrated hydrochloride to "pH" 1-2. The white precipitate was collected by filtration and dried to give the title compound as a white solid (4 g).
m/z (M+H)⁺: 571

EXAMPLE 8

Preparation of chiral (2'S, 3S, 4'R)-6-chloro-4'-[5-chloro-2-(1-hydroxycarbonyl-1-methyl-ethoxy)-phenyl]-2'-(5-fluoro-2-methyl-phenyl)-6'-thioxo spiro[3H-indole-3,3'-piperidine]-2(1H)-one

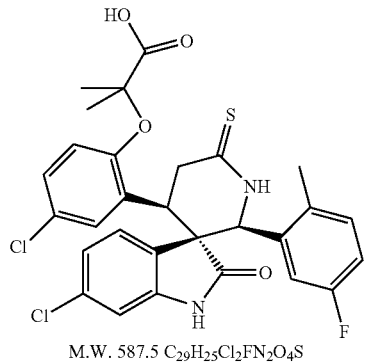

M.W. 587.5 C₂₉H₂₅Cl₂FN₂O₄S

A mixture of chiral (2'S, 3S, 4'R)-6-chloro-4'-[5-chloro-2-(1-hydroxycarbonyl-1-methyl-ethoxy)-phenyl]-2'-(5-fluoro-2-methyl-phenyl) spiro[3H-indole-3,3'-piperidine]-2,6'(1H)-dione (30 mg, 0.052 mmol) and Lawesson's Reagent (40 mg, 0.09 mmol) in THF (1 mL) was stirred at room temperature for 3 h, then purified by flash column to give the title compound as white solid (7 mg).

EXAMPLE 9

Preparation of racemic (2'S, 3S, 4'R)-6-chloro-4'-[5-chloro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one

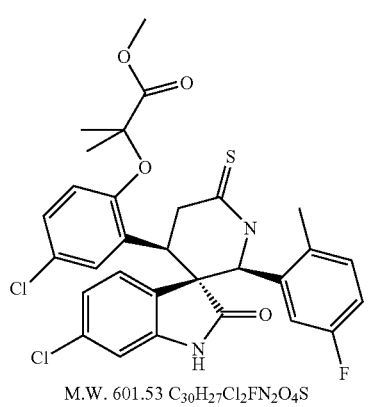

M.W. 601.53 C₃₀H₂₇Cl₂FN₂O₄S

A mixture of racemic (2'S, 3S, 4'R)-6-chloro-4'-[5-chloro-2-(1-methoxycarbonyl-1-methyl-ethoxy)-phenyl]-2'-(5-fluoro-2-methyl-phenyl) spiro[3H-indole-3,3'-piperidine]-2,6'(1H)-dione (200 mg, 0.34 mmol) prepared in Example 5 and Lawesson's Reagent (270 mg, 0.61 mmol) in THF (5 mL) was stirred at room temperature for 1 h, then purified by flash column chromatography to give the title compound as white solid (130 mg).

EXAMPLE 10

Preparation of chiral (2'S, 3S, 4'R)-6-chloro-4'-[5-chloro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one

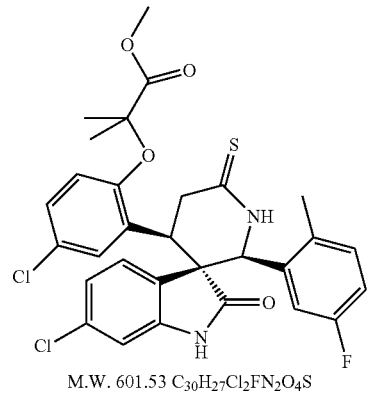

M.W. 601.53 C₃₀H₂₇Cl₂FN₂O₄S

A mixture of chiral (2'S, 3S, 4'R)-6-chloro-4'-[5-chloro-2-(1-methoxycarbonyl-1-methyl-ethoxy)-phenyl]-2'-(5-fluoro-2-methyl-phenyl) spiro[3H-indole-3,3'-piperidine]-2,6'(1H)-dione (300 mg, 0.52 mmol) prepared in Example 6 and P₂S₅ (227 mg, 1.02 mmol) in THF (3 mL) was heated at 40° C. for 2 h, and then diluted with toluene (20 mL). The mixture was concentrated in vacuo and the residue was washed with DCM twice. The DCM solution was collected and purified by flash column chromatography to give the title compound as white solid (260 mg).

EXAMPLE 11

Preparation of intermediate 2-(4-chloro-2-formyl-phenoxy)-butyric acid methyl ester

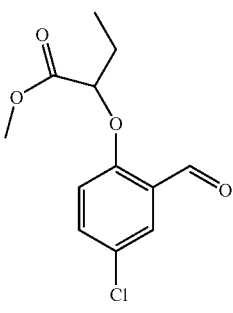

M.W. 256.69 C₁₂H₁₃ClO₄

A mixture of 5-chloro-2-hydroxy-benzaldehyde (156 g, 1 mol), 2-bromo-butyric acid methyl ester (271 g, 1.5 mol), KI (2 g, 0.012 mol) and K₂CO₃ (276 g, 2 mol) in DMF (500 mL) was heated at 130° C. for 2 h. After cooled to room temperature, the mixture was concentrated. The residue was partitioned between EtOAc and water. The organic layer was washed with water, brine, dried over anhydrous Na$_2$SO$_4$ and concentrated to give the title compound (240 g).

EXAMPLE 12

Preparation of intermediate of 2-(4-chloro-2-[1,3]dioxolan-2-yl-phenoxy)-butyric acid methyl ester

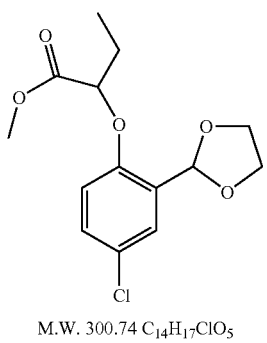

M.W. 300.74 C$_{14}$H$_{17}$ClO$_5$

A mixture of 2-(4-chloro-2-formyl-phenoxy)-butyric acid methyl ester (50 g, 0.195 mol), ethylene glycol (89 mL, 1.56 mol) and p-toluenesulfonic acid (2.8 g, 16.5 mmol) in toluene (400 mL) was refluxed with a Dean-Stark trap attached to remove the water. After 3 h, the reaction was cooled and washed with water, saturated NaHCO$_3$ and water, dried over anhydrous Na$_2$SO$_4$ and concentrated to give the title compound as a light yellow oil (40 g).

EXAMPLE 13

Preparation of intermediate of 2-(4-chloro-2-[1,3]dioxolan-2-yl-phenoxy)-2-ethyl-butyric acid methyl ester

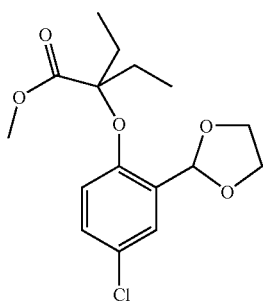

M.W. 328.80 C$_{16}$H$_{21}$ClO$_5$

Lithium bis(trimethylsilyl)amide (60 mL, 60 mmol, 1 M in THF) was slowly added to a solution of 2-(4-chloro-2-[1,3]dioxolan-2-yl-phenoxy)-butyric acid methyl ester (15 g, 50 mmol) in anhydrous THF (150 mL) at −78° C. After the mixture was stirred for 15 min, iodoethane (9.3 g, 60 mmol) was added. The mixture was allowed to warm to room temperature and stirred for 2 h. Then the mixture was diluted with ethyl acetate, washed with a saturated aqueous solution of NH$_4$Cl, dried over anhydrous Na$_2$SO$_4$ and concentrated to give the crude product as a oil (16 g).

EXAMPLE 14

Preparation of intermediate of 2-(4-chloro-2-formyl-phenoxy)-2-ethyl-butyric acid methyl ester

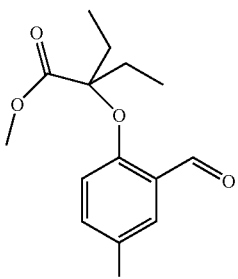

M.W 284.74 C$_{14}$H$_{17}$ClO$_4$

A solution of 2-(4-chloro-2-[1,3]dioxolan-2-yl-phenoxy)-2-ethyl-butyric acid methyl ester (16 g, 48.8 mmol) in trifluoroacetic acid (20 mL) was stirred at room temperature for 3 h. Then the mixture was concentrated and the residue was partitioned between EtOAc and water. The organic layer was washed with 1N NaOH solution, water, dried over anhydrous Na$_2$SO$_4$ and concentrated to give the title compound (13 g).

EXAMPLE 15

Preparation of intermediate E/Z-2-[4-chloro-2-(6-chloro-2-oxo-1,2-dihydro-indol-3-ylidenemethyl)-phenoxy]-2-ethyl-butyric acid methyl ester

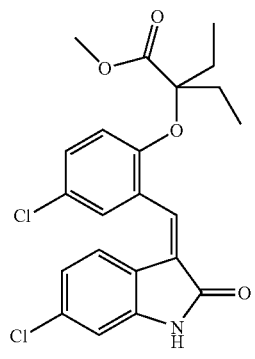

M.W 434.32 C$_{22}$H$_{21}$Cl$_2$NO$_4$

To the mixture of 6-chlorooxindole (8.3 g, 49.7 mmol) and 2-(4-chloro-2-formyl-phenoxy)-2-ethyl-butyric acid methyl ester (13 g, 45.8 mmol) in methanol (200 mL) was added pyrrolidine (4.1 mL, 49.7 mmol) dropwise. The mixture was then heated at 70° C. for 2 h. After cooled to room temperature, the mixture was filtered and the precipitate was collected, dried to give the title compound as a yellow solid (15.5 g).

EXAMPLE 16

Preparation of intermediate E/Z-3-[5-chloro-2-(1-ethyl-1-methoxycarbonyl-prop oxy)-benzylidene]-6-chloro-2-oxo-2,3-dihydro-indole-1-carboxylic acid tert-butyl ester

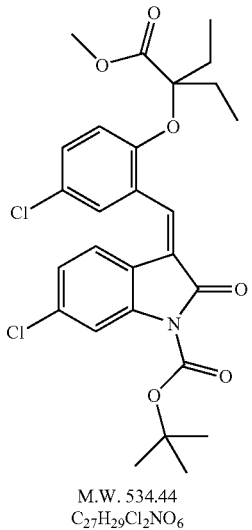

M.W. 534.44
$C_{27}H_{29}Cl_2NO_6$

To a solution of E/Z-2-[4-chloro-2-(6-chloro-2-oxo-1,2-dihydro-indol-3-ylidenemethyl)-phenoxy]-2-ethyl-butyric acid methyl ester (15.5 g, 36 mmol) in dichloromethane (200 mL) at room temperature was added di-tert-butyl-dicarbonate (8.6 g, 39 mmol), followed by the addition of 4-dimethylaminopyridine (0.4 g, 3.3 mmol). After the reaction mixture was stirred at room temperature for 1 h, the solution was washed with 1 M HCl and brine twice, dried over anhydrous $Na_2SO_4$ and concentrated to give the title compound as a yellow solid (15 g).

EXAMPLE 17

Preparation of intermediate racemic (2'S, 3S, 4'R)-6-chloro-4'-[5-chloro-2-(1-ethyl-1-methoxycarbonyl-propoxy)-phenyl]-2'-(5-fluoro-2-methyl-phenyl) spiro[3H-indole-3,3'-piperidine]-2,6'(1H)-dione

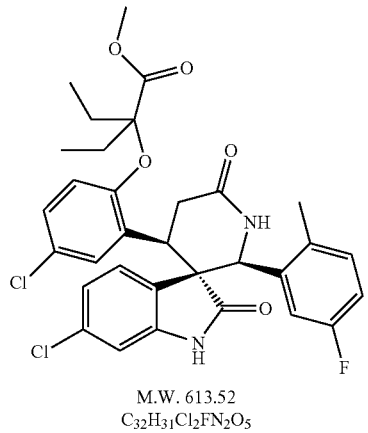

M.W. 613.52
$C_{32}H_{31}Cl_2FN_2O_5$

A mixture of E/Z-3-[5-chloro-2-(1-methoxycarbonyl-1-ethyl-propoxy)-benzylidene]-6-chloro-2-oxo-2,3-dihydro-indole-1-carboxylic acid tert-butyl ester (7.6 g, 15 mmol) and 1-(5-fluoro-2-methyl-phenyl)-3-trimethylsilyoxy-2-aza-1,3-butadiene (60 mmol) prepared in Example 4 in toluene (60 mL) was heated at 60° C. for 3 h, and concentrated in vacuo. To the residue was added DCM (50 mL) and TFA (20 mL), and the resulting solution was stirred at room temperature for 3 h, then concentrated in vacuo, partitioned between ethyl acetate and diluted aqueous NaOH solution. The organic layer was washed with water, dried over anhydrous $Na_2SO_4$, and concentrated. The residue was purified by flash column chromatography to give the title compound as white solid (2.2 g).

m/z (M+H)$^+$: 613

EXAMPLE 18

Preparation of intermediate racemic (2'S, 3S, 4'R)-6-chloro-4'-[5-chloro-2-(1-ethyl-1-hydroxycarbonyl-propoxy)-phenyl]-2'-(5-fluoro-2-methyl-phenyl) spiro[3H-indole-3,3'-piperidine]-2,6'(1H)-dione

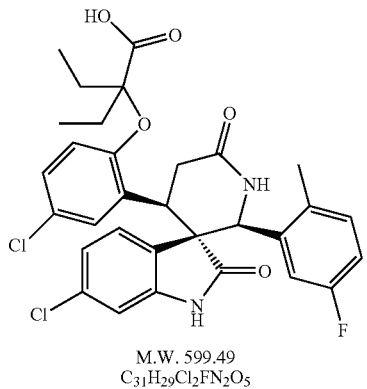

M.W. 599.49
$C_{31}H_{29}Cl_2FN_2O_5$

A mixture of racemic (2'S, 3S, 4'R)-6-chloro-4'-[5-chloro-2-(1-ethyl-1-methoxycarbonyl-propoxy)-phenyl]-2'-(5-fluoro-2-methyl-phenyl) spiro[3H-indole-3,3'-piperidine]-2,6'(1H)-dione (200 mg, 0.33 mmol), LiOH.H$_2$O (69 mg, 1.16 mmol), H$_2$O (2 mL) and methanol (20 mL) was refluxed for 2 h. After cooled to room temperature, the solution was concentrated and the residue was acidified to "pH" 2-3 by addition of concentrated HCl solution. The precipitate was collected by filtration to give the title compound as a white solid (57 mg).

m/z (M+H)$^+$: 599

EXAMPLE 19

Preparation of intermediate racemic (2'S, 3S, 4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione

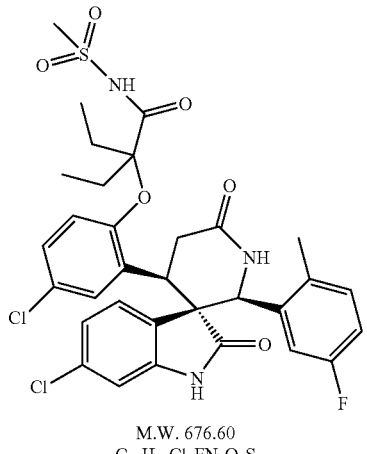

M.W. 676.60
$C_{32}H_{32}Cl_2FN_3O_6S$

A solution of racemic (2'S, 3S, 4'R)-6-chloro-4'-[5-chloro-2-(1-ethyl-1-hydroxycarbonyl-propoxy)-phenyl]-2'-(5-fluoro-2-methyl-phenyl) spiro[3H-indole-3,3'-piperidine]-2,6'(1H)-dione (30 mg, 0.05 mmol) and CDI (20 mg, 0.12 mmol) in DMF (1 mL) was heated at 60° C. for 2 h. Then to this solution was added a mixture of methanesulfonamide (28 mg, 0.3 mmol) and NaH (12 mg, 60%, 0.3 mmol) in DMF (1 mL), which had been stirred for 2 h at room temperature. After the resulting mixture was stirred at room temperature for 1 h, it was poured into water and the aqueous solution was acidified to "pH" 1-2 by addition of concentrated HCl solution. The aqueous phase was extracted with EtOAc twice, The combined organic phases were dried over anhydrous Na$_2$SO$_4$, concentrated and the residue was purified by flash column to give the title compound as a white solid (10 mg).

m/z (M+H)$^+$: 676

EXAMPLE 20

Preparation of intermediate racemic (2'S, 3S, 4'R)-1-acetyl-6-chloro-4'-[5-chloro-2-(2-methanesulfonylamino-1,1-diethyl-2-oxo-ethoxy)-phenyl]-2'-(5-fluoro-2-methyl-phenyl)-spiro[3H-indole-3,3'-piperidine]-2,6'(1H)-dione

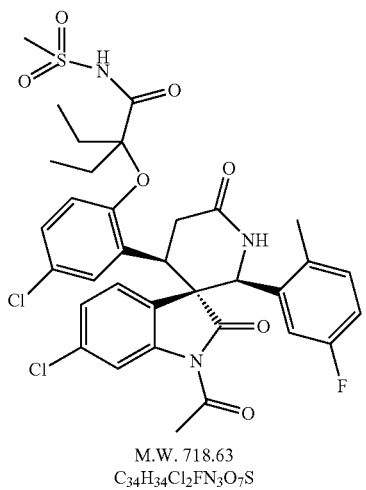

M.W. 718.63
C$_{34}$H$_{34}$Cl$_2$FN$_3$O$_7$S

At room temperature, to a mixture of racemic (2'S, 3S, 4'R)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione (540 mg, 0.8 mmol) and acetic anhydride (98 mg, 0.96 mmol) in DCM (20 mL) was added DMAP (10 mg, 0.08 mmol) slowly. After the mixture was stirred for 2 h, the solution was washed by 0.5N HCl solution twice, dried over anhydrous Na$_2$SO$_4$ and concentrated. The residue was purified by flash column chromatography to give the title compound as a white solid (450 mg).

EXAMPLE 21

Preparation of intermediate chiral (2'S, 3S, 4'R)-1-acetyl-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione

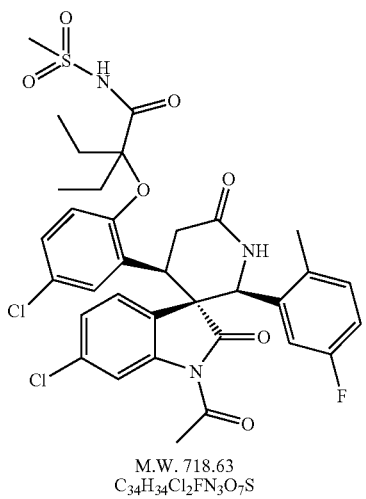

M.W. 718.63
C$_{34}$H$_{34}$Cl$_2$FN$_3$O$_7$S

Separation of the two enantiomers from racemic (2'S, 3S, 4'R)-1-acetyl-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione (50 mg), was conducted by chiral SFC to provide chiral (2'S, 3S, 4'R)-1-acetyl-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione
as a white solid (15 mg).
m/z (M+H)$^+$: 718

EXAMPLE 22

Preparation of intermediate chiral (2'R, 3R, 4'S)-1-acetyl-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione

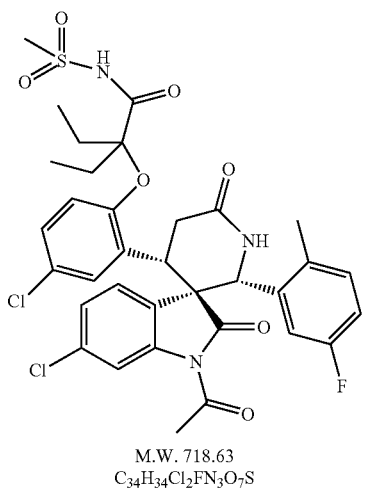

M.W. 718.63
C$_{34}$H$_{34}$Cl$_2$FN$_3$O$_7$S

In the SFC chiral separation of the two enantiomers from racemic (2'S, 3S, 4'R)-1-acetyl-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione (50 mg) in Example 21, chiral (2'R, 3R, 4'S)-1-acetyl-6-chloro-4'-[5-chloro-2-(1-ethyl-1-methane-sulfonylaminocarbonyl-propoxy)-phenyl]-2'-(5-fluoro-2-methyl-phenyl)-spiro[3H-indole-3,3'-piperidine]-2,6'(1H)-dione was obtained as a white solid (17 mg).

m/z (M+H)⁺: 718

EXAMPLE 23

Preparation of intermediate chiral (2'S, 3S, 4'R)-1-acetyl-6-chloro-4'-[5-chloro-2-(2-methanesulfony-lamino-1,1-diethyl-2-oxo-ethoxy)-phenyl]-2'-(5-fluoro-2-methyl-phenyl)-6'-thioxo spiro[3H-indole-3,3'-piperidine]-2(1H)-one

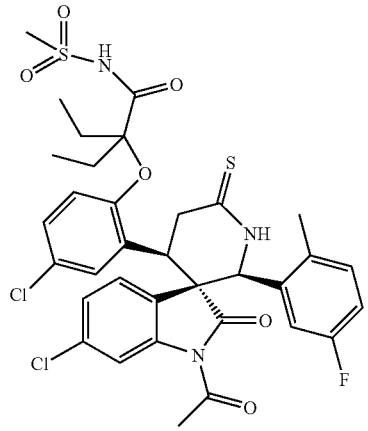

M.W 734.7
$C_{34}H_{34}Cl_2FN_3O_6S_2$

A mixture of chiral (2'S, 3S, 4'R)-1-acetyl-6-chloro-4'-[5-chloro-2-(2-methanesulfonylamino-1,1-diethyl-2-oxo-ethoxy)-phenyl]-2'-(5-fluoro-2-methyl-phenyl)-spiro[3H-indole-3,3'-piperidine]-2,6'(1H)-dione (50 mg, 0.07 mmol) and Lawesson's Reagent (56 mg, 0.126 mmol) in toluene (5 mL) was heated at 125° C. for 1.5 h. The mixture was purified by flash column chromatography to give the title compound as white solid (15 mg).

EXAMPLE 24

Preparation of chiral (2'S, 3S, 4'R)-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one

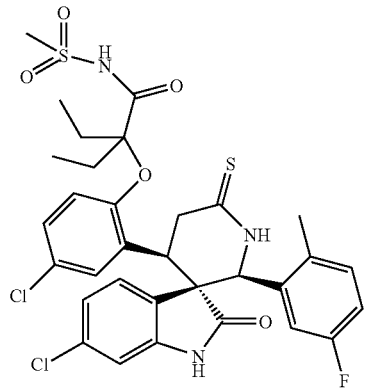

M.W 692.66
$C_{32}H_{32}Cl_2FN_3O_5S_2$

A mixture of chiral (2'S, 3S, 4'R)-1-acetyl-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one (45 mg) and $K_2CO_3$ (30 mg) in methanol (2 mL) was stirred at room temperature for 15 min, and then the mixture was partitioned between ethyl acetate and diluted aqueous HCl solution. The organic layer was washed with brine, dried over anhydrous $Na_2SO_4$, concentrated to give the title compound as white solid (35 mg).

EXAMPLE 25

Preparation of intermediate chiral (2'S, 3S, 4'R)-6-chloro-4'-[5-chloro-2-(1-ethyl-1-methanesulfony-laminocarbonyl-propoxy)-phenyl]-2'-(5-fluoro-2-methyl-phenyl)-spiro[3H-indole-3,3'-piperidine]-2,6'(1H)-dione

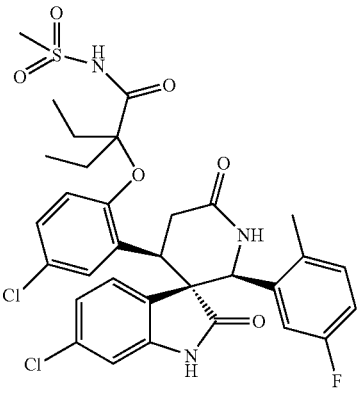

M.W 676.60
$C_{32}H_{32}Cl_2FN_3O_6S$

Separation of the two enantiomers from racemic (2'S, 3S, 4'R)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione (12 g), was conducted by chiral SFC to provide chiral (2'S, 3S, 4'R)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione as a white solid (5 g).

m/z (M+H)⁺: 676

EXAMPLE 26

Preparation of intermediate chiral (2'R, 3R, 4'S)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione

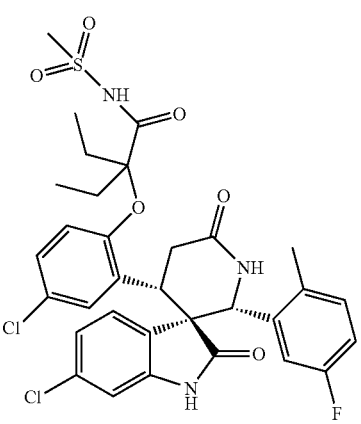

M.W 676.60
$C_{32}H_{32}Cl_2FN_3O_6S$

In the SFC chiral separation of the two enantiomers from racemic (2'S, 3S, 4'R)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione (12 g) in Example 25, chiral (2'R, 3R, 4'S)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione was obtained as a white solid (5 g).

EXAMPLE 27

Preparation of chiral (2'R, 3R, 4'S)-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one

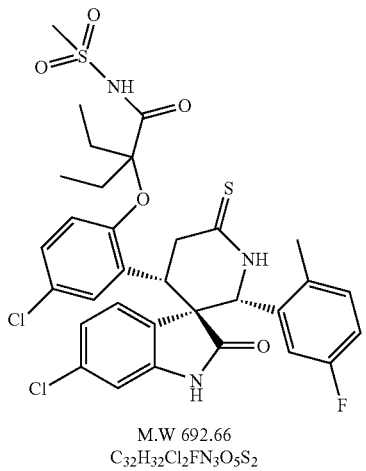

M.W 692.66
$C_{32}H_{32}Cl_2FN_3O_5S_2$

A mixture of chiral (2'R, 3R, 4'S)-4'-[5-chloro-2-(2-methanesulfonylamino-1,1-diethyl-2-oxo-ethoxy)-phenyl]-6-chloro-2'-(5-fluoro-2-methyl-phenyl)-spiro[3H-indole-3,3'-piperidine]-2,6'(1H)-dione (200 mg, 0.3 mmol) and $P_2S_5$ (130 mg, 0.6 mmol) was heated at 60° C. for 1 h, and then diluted with toluene (20 mL). The mixture was concentrated in vacuo and the residue was washed with DCM for 2 times. The DCM solution was collected and purified by flash column to give the title compound as white solid (121 mg).

EXAMPLE 28

Preparation of intermediate 1-(5-chloro-2-methylphenyl)-3-trimethylsilyoxy-2-aza-1,3-butadiene

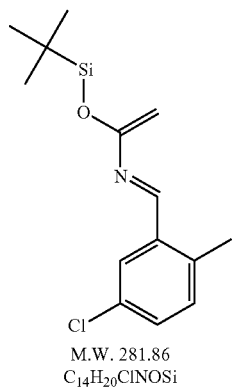

M.W. 281.86
$C_{14}H_{20}ClNOSi$

To dry tetrahydrofuran (100 mL) was added 1M THF solution of LiHMDS (97 mmol, 97 mL) under Ar at room temperature, followed by the addition of 5-chloro-2-methyl-benzaldehyde (15 g, 97 mmol). After the mixture was stirred at room temperature for 1 h, trimethylsilyl chloride (12.3 mL, 97 mmol) was added dropwise. Then the temperature of the mixture was lowered to 0° C. on a cooling ice bath. To this mixture was added triethylamine (17.6 mL, 126 mmol) in one portion, followed by the dropwise addition of a solution of acetyl chloride (9 mL, 126 mmol) in diethyl ether (200 mL). The cooling bath was removed, and the mixture was stirred at room temperature overnight. The mixture was quickly filtered on celite under nitrogen, and filtrate was concentrated under reduced pressure to give crude 1-(5-chloro-2-methylphenyl)-3-trimethylsilyoxy-2-aza-1,3-butadiene as a yellow gum and used for the next step without further purification.

EXAMPLE 29

Preparation of intermediate racemic (2'S, 3S, 4'R)-6-chloro-4'-[5-chloro-2-(1-ethyl-1-methoxycarbonyl-propoxy)-phenyl]-2'-(5-chloro-2-methyl-phenyl) spiro[3H-indole-3,3'-piperidine]-2,6'(1H)-dione

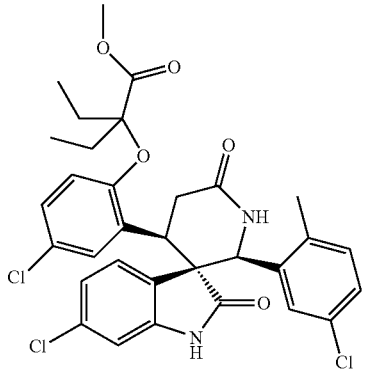

M.W 629.97
$C_{32}H_{31}Cl_3N_2O_5$

A mixture of E/Z-3-[5-chloro-2-(1-methoxycarbonyl-1-ethyl-propoxy)-benzylidene]-6-chloro-2-oxo-2,3-dihydro-indole-1-carboxylic acid tert-butyl ester (2.63 g, 4.9 mmol) prepared in Example 16 and 1-(5-chloro-2-methylphenyl)-3-trimethylsilyoxy-2-aza-1,3-butadiene (20 mmol) in toluene (20 mL) was heated at 60° C. for 3 h, and concentrated in vacuo. To the residue was added DCM (20 mL) and TFA (10 mL), and the resulting solution was stirred at room temperature for 3 h, then concentrated, partitioned between ethyl acetate and diluted aqueous NaOH solution. The organic layer was separated, washed with water, dried over anhydrous $Na_2SO_4$, and concentrated. The residue was purified by flash column chromatography to give the title compound as white solid (600 mg).

m/z (M+H)$^+$: 629

EXAMPLE 30

Preparation of intermediate racemic (2'S, 3S, 4'R)-6-chloro-4'-[5-chloro-2-(1-ethyl-1-hydroxycarbonyl-propoxy)-phenyl]-2'-(5-chloro-2-methyl-phenyl) spiro[3H-indole-3,3'-piperidine]-2,6'(1H)-dione

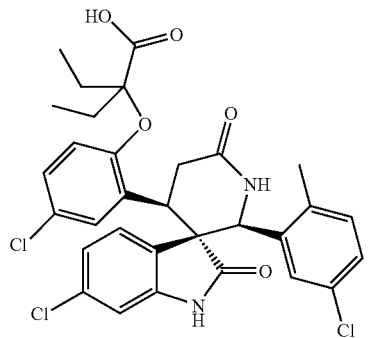

M.W. 615.95
$C_{31}H_{29}Cl_3N_2O_5$

A mixture of racemic (2'S, 3S, 4'R)-6-chloro-4'-[5-chloro-2-(1-ethyl-1-methoxycarbonyl-propoxy)-phenyl]-2'-(5-chloro-2-methyl-phenyl) spiro[3H-indole-3,3'-piperidine]-2,6'(1H)-dione (100 mg, 0.159 mmol), LiOH (19.87 mg, 0.8 mmol), $H_2O$ (2 mL) and methanol (3 mL) was heated at 40° C. for 4 h. Then methanol was removed under reduced pressure. The aqueous solution was acidified to "pH" 1-2 by addition of concentrated hydrochloride acid. The precipitate was collected by filtration and purified by Prep-HPLC to give the title compound as a white solid (50 mg).

m/z (M+H)$^+$: 615

EXAMPLE 31

Preparation of intermediate racemic (2'S, 3S, 4'R)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

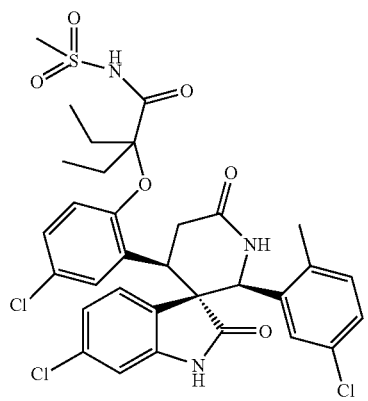

M.W 693.05
$C_{32}H_{32}Cl_3N_3O_6S$

A solution of racemic (2'S, 3S, 4'R)-6-chloro-4'-[5-chloro-2-(1-hydroxycarbonyl-1-ethyl-propoxy)-phenyl]-2'-(5-chloro-2-methyl-phenyl) spiro[3H-indole-3,3'-piperidine]-2,6'(1H)-dione (150 mg, 0.244 mmol) and CDI (80 mg, 0.49 mmol) in DMF (2 mL) was heated at 60° C. for 2 h. Then to this solution was added a mixture of methanesulfonamide (231 mg, 2.44 mmol) and NaH (78 mg, 60%, 1.95 mmol) in DMF (3 mL), which had been stirred at room temperature for 2 h. After stirred at room temperature for 1 h, the reaction mixture was poured into water and acidified to "pH" 2-3 by addition of aqueous concentrated HCl solution. The mixture was partitioned between ethyl acetate and water. The organic layer was separated, and the aqueous layer was extracted with ethyl acetate twice. The combined organic extracts were dried over anhydrous $Na_2SO_4$, concentrated and the residue was purified by flash column chromatography to give the title compound as a white solid (10 mg).

m/z (M+H)$^+$: 692

EXAMPLE 32

Preparation of intermediate racemic (2'S, 3S, 4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

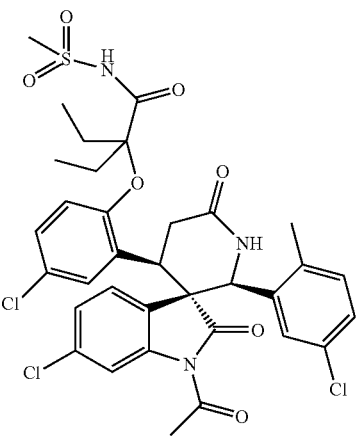

M.W. 735.09
$C_{34}H_{34}Cl_3N_3O_7S$

At room temperature, to a mixture of racemic (2'S, 3S, 4'R)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (400 mg, 0.58 mmol) and acetic anhydride (71 mg, 0.69 mmol) in DCM (20 mL) was added DMAP (7 mg, 0.06 mmol) slowly. After the mixture was stirred for 2 h, the solution was washed by 0.5N HCl solution twice, dried over anhydrous $Na_2SO_4$ and concentrated. The residue was purified by Prep-HPLC to give the title compound as a white solid (100 mg).

EXAMPLE 33

Preparation of intermediate chiral (2'S, 3S, 4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

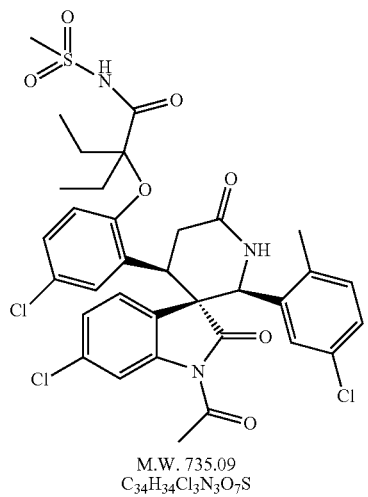

M.W. 735.09
C₃₄H₃₄Cl₃N₃O₇S

Separation of the two enantiomers from racemic (2'S, 3S, 4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (50 mg) was conducted by chiral SFC to provide chiral (2'S, 3S, 4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione as a white solid (15 mg)

m/z (M+H)⁺: 734

EXAMPLE 34

Preparation of intermediate chiral (2'R, 3R, 4'S)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

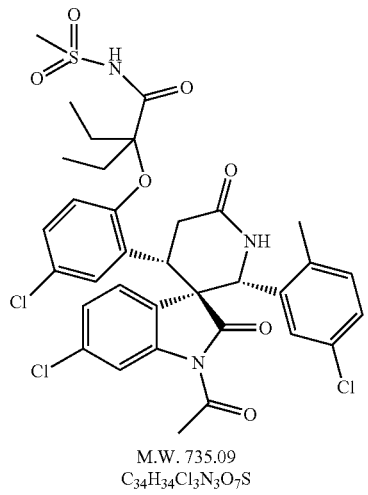

M.W. 735.09
C₃₄H₃₄Cl₃N₃O₇S

In SFC chiral separation of the two enantiomers from racemic (2'S, 3S, 4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (50 mg) in Example 33, chiral (2'R, 3R, 4'S)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione was obtained as a white solid (15 mg).

m/z (M+H)⁺: 734

EXAMPLE 35

Preparation of chiral (2'S, 3S, 4'R)-6-chloro-4'-[5-chloro-2-(2-methanesulfonylamino-1,1-diethyl-2-oxo-ethoxy)-phenyl]-2'-(5-chloro-2-methyl-phenyl)-6'-thioxo spiro[3H-indole-3,3'-piperidine]-2(1H)-one

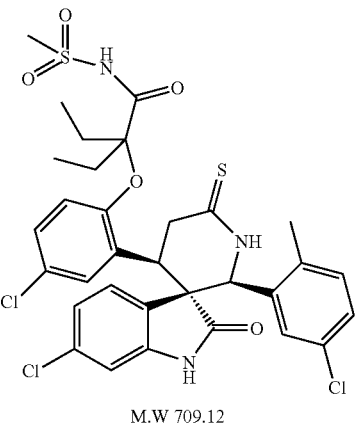

M.W 709.12
C₃₂H₃₂Cl₃N₃O₅S₂

A mixture of chiral (2'S, 3S, 4'R)-1-acetyl-6-chloro-2'-(5-chloro-2-methyl-phenyl)-4'-[5-chloro-2-(2-methanesulfonylamino-1,1-diethyl-2-oxo-ethoxy)-phenyl]-spiro[3H-indole-3,3'-piperidine]-2,6'(1H)-dione (30 mg, 0.04 mmol) and P₂S₅ (26 mg, 0.12 mmol) in THF (2 mL) was stirred at room temperature overnight, then diluted with toluene (10 mL). The resultant mixture was concentrated and washed with DCM for two times. The DCM solution was collected and purified by flash column chromtography. The product was then stirred with K₂CO₃ (20 mg) in MeOH for 15 min, and then partitioned between ethyl acetate and diluted HCl solution. The organic layer was washed with brine, dried over anhydrous Na₂SO₄ and concentrated to give the title product as white solid (25 mg).

EXAMPLE 36

Preparation of intermediate 2-(4-chloro-2-formyl-phenoxy)-pentanoic acid ethyl ester

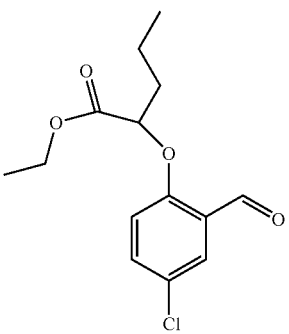

M.W 284.74
C₁₄H₁₇ClO₄

A mixture of 5-chloro-2-hydroxy-benzaldehyde (15 g, 0.1 mol), 2-bromo-pentanoic acid ethyl ester (27 g, 0.13 mol) and K$_2$CO$_3$ (27 g, 0.2 mol) in DMF (100 mL) was heated at 140° C. for 1 h. After cooled to room temperature, the mixture was poured into water and the aqueous phase was extrated with EtOAc thrice. The combined organic phases were washed with water and brine, dried over anhydrous Na$_2$SO$_4$ and concentrated. The residue was purified by flash column to give the title compound as a colorless oil (24 g).

EXAMPLE 37

Preparation of intermediate 2-(4-chloro-2-[1,3]dioxolan-2-yl-phenoxy)-pentanoic acid ethyl ester

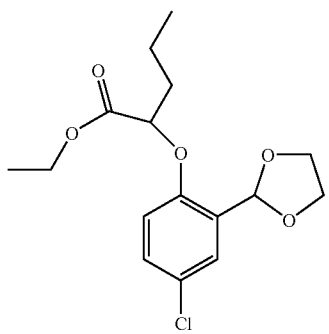

M.W 328.80
C$_{16}$H$_{21}$ClO$_5$

A mixture of 2-(4-chloro-2-formyl-phenoxy)-pentanoic acid ethyl ester (15 g, 53 mmol), ethylene glycol (25 mL, 440 mmol) and p-toluenesulfonic acid (0.8 g, 4.65 mmol) in toluene (150 mL) was refluxed with a Dean-Stark trap attached to remove water. After 3 h, the reaction was cooled and washed with water, saturated NaHCO$_3$ solution and water, dried over anhydrous Na$_2$SO$_4$ and concentrated to give the title compound as a light yellow oil (16 g).

EXAMPLE 38

Preparation of intermediate 2-(4-chloro-2-[1,3]dioxolan-2-yl-phenoxy)-2-propyl-pentanoic acid ethyl ester

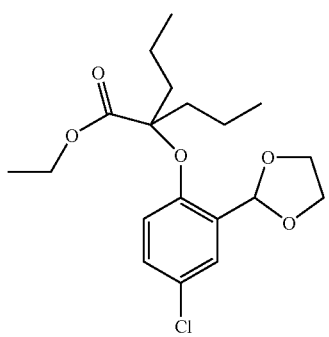

M.W 370.88
C$_{19}$H$_{27}$ClO$_5$

Lithium bis(trimethylsilyl)amide (26 mL, 26 mmol, 1 M in THF) was slowly added to a solution of 2-(4-Chloro-2-[1,3] dioxolan-2-yl-phenoxy)-pentanoic acid ethyl ester (6.6 g, 20 mmol) in 60 mL of anhydrous THF at −78° C. After the mixture was stirred for 30 min at −78° C., 1-Iodopropane (4 mL, 40 mmol) was added. The mixture was allowed to warm to room temperature and stirred for 2 h. Then the mixture was diluted with ethyl acetate, washed with a saturated aqueous solution of NH$_4$Cl, dried over anhydrous Na$_2$SO$_4$ and concentrated to give the title compound as a yellow oil (5 g).

EXAMPLE 39

Preparation of intermediate 2-(4-chloro-2-formyl-phenoxy)-2-propyl-pentanoic acid ethyl ester

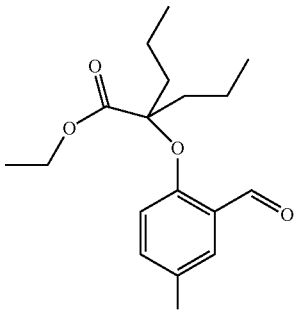

M.W 326.82
C$_{17}$H$_{23}$ClO$_4$

A solution of 2-(4-chloro-2-[1,3]dioxolan-2-yl-phenoxy)-2-propyl-pentanoic acid ethyl ester (15 g, 42 mmol) in TFA (30 mL) was stirred at room temperature overnight. Then the mixture was concentrated and the residue was partitioned between EtOAc and water. The organic phase was washed with 1N NaOH solution, water, dried over anhydrous Na$_2$SO$_4$ and concentrated to give the title compound (14 g).

EXAMPLE 40

Preparation of intermediate E/Z-2-[4-chloro-2-(6-chloro-2-oxo-1,2-dihydro-indol-3-ylidenemethyl)-phenoxy]-2-propyl-pentanoic acid ethyl ester

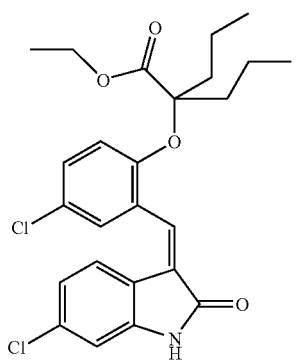

M.W 476.40
C$_{25}$H$_{27}$Cl$_2$NO$_4$

To the mixture of 6-chlorooxindole (9.3 g, 55.7 mmol) and 2-(4-chloro-2-formyl-phenoxy)-2-propyl-pentanoic acid ethyl ester (14 g, 42.9 mmol) in methanol (100 mL) was added pyrrolidine (3.3 g, 47.2 mmol) dropwise. The mixture was then heated at 80° C. for 2 h. After cooled to room temperature, the mixture was concentrated. The residue was purified by flash column to give the title compound (4.2 g).

EXAMPLE 41

Preparation of intermediate E/Z-6-chloro-3-[5-chloro-2-(1-ethoxycarbonyl-1-propyl-butoxy)-benzylidene]-2-oxo-2,3-dihydro-indole-1-carboxylic acid tert-butyl ester

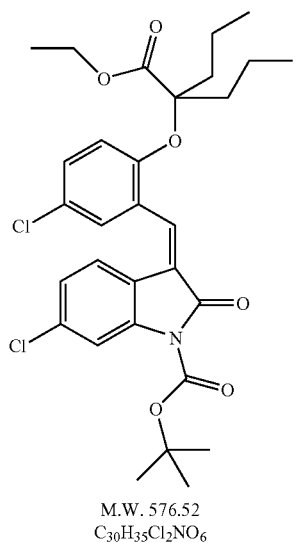

M.W. 576.52
$C_{30}H_{35}Cl_2NO_6$

To a solution of E/Z-2-[4-chloro-2-(6-chloro-2-oxo-1,2-dihydro-indol-3-ylidenemethyl)-phenoxy]-2-propyl-pentanoic acid ethyl ester (4.2 g, 8.8 mmol) in dichloromethane (100 mL) at room temperature was added di-tert-butyl-dicarbonate (2.2 g, 9.68 mmol), followed by the addition of 4-dimethylaminopyridine (0.5 g, 4.1 mmol). After the reaction mixture was stirred at room temperature for 1 h, the solution was concentrated. The residue was purified by flash column to give the title compound as a yellow solid (2.6 g).

EXAMPLE 42

Preparation of intermediate racemic (2'S, 3S, 4'R)-6-chloro-4'-[5-chloro-2-(1-ethoxycarbonyl-1-propyl-butoxy)-phenyl]-2'-(5-fluoro-2-methyl-phenyl) spiro[3H-indole-3,3'-piperidine]-2,6'(1H)-dione

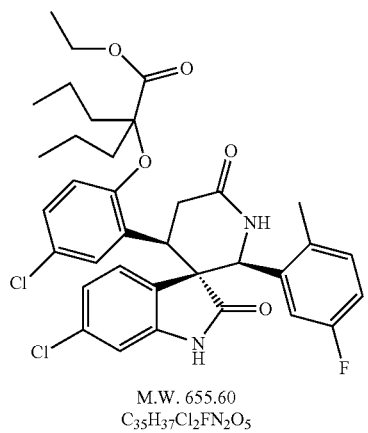

M.W. 655.60
$C_{35}H_{37}Cl_2FN_2O_5$

A mixture of E/Z-6-Chloro-3-[5-chloro-2-(1-ethoxycarbonyl-1-propyl-butoxy)-benzylidene]-2-oxo-2,3-dihydro-indole-1-carboxylic acid tert-butyl ester (1.3 g, 2.3 mmol) and 1-(5-fluoro-2-methyl-phenyl)-3-trimethylsilyoxy-2-aza-1,3-butadiene (10 mmol) prepared in Example 28 in toluene (10 mL) was heated at 60° C. for 3 h, and concentrated in vacuo. To the residue was added DCM (20 mL) and TFA (5 mL), and the resultant solution was stirred at room temperature for 3 h, then concentrated in vacuo, partitioned between ethyl acetate and diluted NaOH solution. The organic layer was washed with water, dried over anhydrous $Na_2SO_4$, concentrated. The residue was purified by flash column chromatography to give the title compound as white solid (150 mg).
m/z (M+H)$^+$: 655

EXAMPLE 43

Preparation of racemic (2'S, 3S, 4'R)-6-chloro-4'-[5-chloro-2-(1-ethoxycarbonyl-1-propyl-butoxy)-phenyl]-2'-(5-fluoro-2-methyl-phenyl)-6'-thioxo spiro[3H-indole-3,3'-piperidine]-2(1H)-one

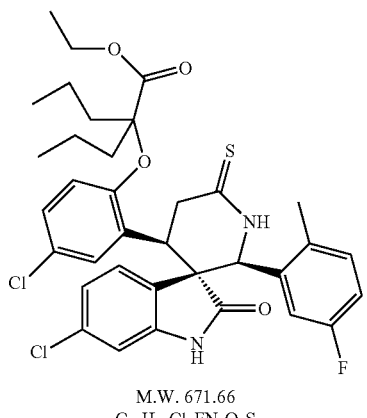

M.W. 671.66
$C_{35}H_{37}Cl_2FN_2O_4S$

A mixture of racemic (2'S, 3S, 4'R)-6-chloro-4'-[5-chloro-2-(1-ethoxycarbonyl-1-propyl-butoxy)-phenyl]-2'-(5-fluoro-2-methyl-phenyl) spiro[3H-indole-3,3'-piperidine]-2,6'(1H)-dione (100 mg, 0.15 mmol) and $P_2S_5$ (70 mg, 0.31 mmol) was heated at 60° C. for 2 h, and then diluted with toluene (10 mL). The mixture was concentrated in vacuo and the residue was washed with DCM for 2 times. The DCM solution was combined and concentrated. The residue was purified by flash column to give the title compound as white solid (65 mg).

EXAMPLE 44

Preparation of intermediate chiral (2'S, 3S, 4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-spiro[3H-indole-3,3'-piperidine]-2,6'(1H)-dione

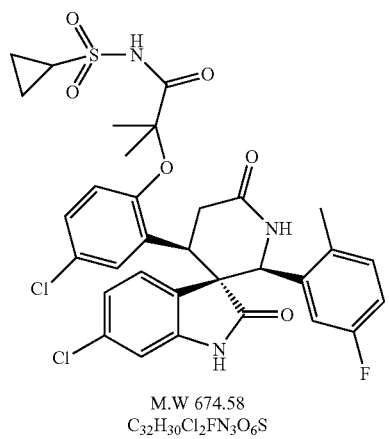

M.W 674.58
$C_{32}H_{30}Cl_2FN_3O_6S$

A solution of chiral (2'S, 3S, 4'R)-6-chloro-4'-[5-chloro-2-(1-hydroxycarbonyl-1-methyl-ethoxy)-phenyl]-2'-(5-fluoro-2-methyl-phenyl) spiro[3H-indole-3,3'-piperidine]-2,6'(1H)-dione (45 mg, 0.079 mmol) prepared in Example 7 and CDI (26 mg, 0.16 mmol) in DMF (0.5 mL) was heated at 60° C. for 2 h. Then to this solution was added a mixture of cyclopropanesulfonamide (48 mg, 0.4 mmol) and NaH (13 mg, 60%, 0.3 mmol) in DMF (1 mL), which had been stirred at room temperature for 1 h. After the resulting mixture was stirred at room temperature for 1 h, it was poured into water (5 mL) and the aqueous solution was acidified to "pH" 2-3 by addition of concentrated aqueous hydrochloride acid. After the aqueous phase was extracted with EtOAc twice, the combined organic phases were dried over anhydrous $Na_2SO_4$, concentrated and the residue was purified by flash column to give the title compound as a white solid (38 mg).

m/z (M+H)$^+$: 674

EXAMPLE 45

Preparation of chiral (2'S, 3S, 4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-6'-thioxo spiro[3H-indole-3,3'-piperidine]-2(1H)-one

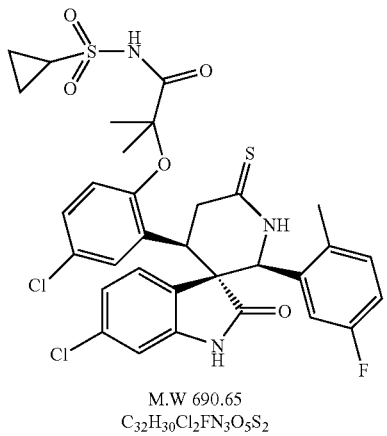

M.W 690.65
$C_{32}H_{30}Cl_2FN_3O_5S_2$

A mixture of chiral (2'S, 3S, 4'R)-4'-[5-chloro-2-(2-cyclopropanesulfonylamino-1,1-dimethyl-2-oxo-ethoxy)-phenyl]-6-chloro-2'-(5-fluoro-2-methyl-phenyl)-spiro[3H-indole-3,3'-piperidine]-2,6'(1H)-dione (12 mg, 0.018 mmol) and $P_2S_5$ (12 mg, 0.054 mmol) in THF (1 mL) was heated at 50° C. for 2 h, and then diluted with toluene (10 mL). The mixture was concentrated in vacuo and the residue was washed with DCM twice. The DCM layers were combined and concentrated. The residue was purified by flash chromatography to give the title compound as white solid (11 mg).

EXAMPLE 46

Preparation of intermediate 1-(4-chloro-2-formyl-phenoxy)-cyclobutanecarboxylic acid methyl ester

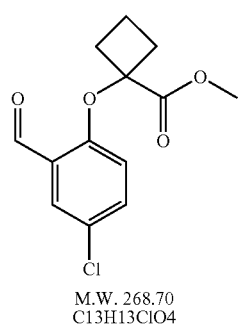

M.W. 268.70
C13H13ClO4

A mixture of 5-chloro-2-hydroxy-benzaldehyde (10 g, 64 mmol), 1-bromo-cyclobutanecarboxylic acid methyl ester (15 g, 77 mmol), $K_2CO_3$ (13 g, 94 mmol) in DMF (100 mL) was heated at 140° C. for 1.5 h. Then the mixture was partitioned between ethyl acetate and water, the organic layer was washed with water 4 times, dried over anhydrous $Na_2SO_4$, concentrated to give crude product as dark oil (18 g).

EXAMPLE 47

Preparation of intermediate E/Z-1-[4-chloro-2-(6-chloro-2-oxo-1,2-dihydro-indol-3-ylidenemethyl)-phenoxy]-cyclobutanecarboxylic acid methyl ester

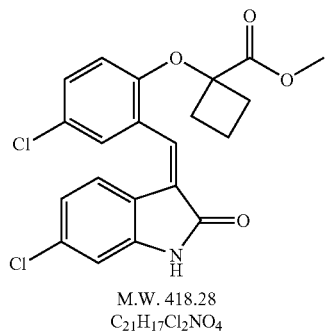

M.W. 418.28
$C_{21}H_{17}Cl_2NO_4$

To the mixture of 6-chlorooxindole (10 g, 60 mmol) and 1-(4-chloro-2-formyl-phenoxy)-cyclobutanecarboxylic acid methyl ester (18 g, 67 mmol) in methanol (100 mL) was added pyrrolidine (4.5 mg, 63 mmol) dropwise. The mixture was then heated at 80° C. for 1 h. After cooled to room temperature, the mixture was filtered and the precipitate was collected, dried to give the title compound (6 g).

EXAMPLE 48

Preparation of intermediate E/Z-6-chloro-3-[5-chloro-2-(1-methoxycarbonyl-cyclobutoxy)-benzylidene]-2-oxo-2,3-dihydro-indole-1-carboxylic acid tert-butyl ester

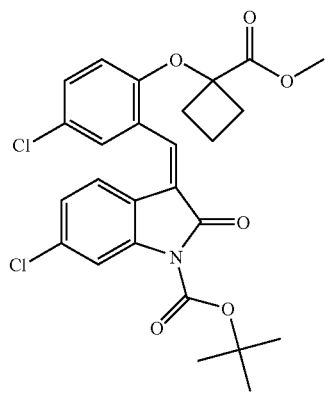

M.W. 518.40
$C_{26}H_{25}Cl_2NO_6$

At room temperature, to a solution E/Z-1-[4-chloro-2-(6-chloro-2-oxo-1,2-dihydro-indol-3-ylidenemethyl)-phenoxy]-cyclobutanecarboxylic acid methyl ester (6 g, 14 mmol) in dichloromethane (100 mL) was added di-tert-butyl-dicarbonate (3.7 g, 16.9 mmol), followed by the addition of 4-dimethylaminopyridine (0.17 g, 1.4 mmol). The reaction mixture was stirred at room temperature for 1 h. Then the mixture was concentrated and the residue was purified by chromatography to give the title compound as an orange solid (5 g).

EXAMPLE 49

Preparation of intermediate racemic (2'S, 3S, 4'R)-6-chloro-4'-[5-chloro-2-(1-methoxycarbonyl-cyclobutoxy)-phenyl]-2'-(5-fluoro-2-methyl-phenyl)-spiro[3H-indole-3,3'-piperidine]-2,6'(1H)-dione

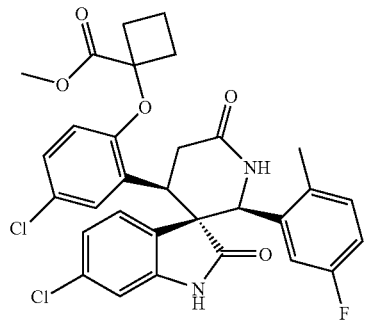

M.W. 597.48
$C_{31}H_{27}Cl_2FN_2O_5$

A mixture of E/Z-6-chloro-3-[5-chloro-2-(1-methoxycarbonyl-cyclobutoxy)-benzylidene]-2-oxo-2,3-dihydro-indole-1-carboxylic acid tert-butyl ester (1.5 g, 2.9 mmol) and 1-(5-fluoro-2-methylphenyl)-3-trimethylsilyoxy-2-aza-1,3-butadiene (10 mmol) prepared in Example 4 in toluene (10 mL) was heated at 60° C. for 3 h. To the mixture was added TFA (5 mL), and the resultant solution was stirred at room temperature for 20 min, then concentrated in vacuo. The residue was partitioned between ethyl acetate and diluted aqueous NaOH solution. The organic layer was separated, washed with water, dried over anhydrous $Na_2SO_4$, and concentrated. The residue was purified by flash chromatography to give the title compound as white solid (200 mg).

EXAMPLE 50

Preparation of racemic (2'S, 3S, 4'R)-6-chloro-4'-[5-chloro-2-(1-methoxycarbonyl-cyclobutoxy)-phenyl]-2'-(5-fluoro-2-methyl-phenyl)-6'-thioxo spiro[3H-indole-3,3'-piperidine]-2(1H)-one

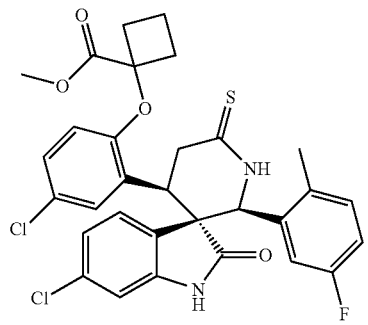

M.W. 613.54
$C_{31}H_{27}Cl_2FN_2O_4S$

A mixture of racemic (2'S, 3S, 4'R)-6-chloro-4'-[5-chloro-2-(1-methoxycarbonyl-cyclobutoxy)-phenyl]-2'-(5-fluoro-2-methyl-phenyl)-spiro[3H-indole-3,3'-piperidine]-2,6'(1H)-dione (30 mg, 0.05 mmol) and $P_2S_5$ (44 mg, 0.2 mmol) in THF (1 mL) was stirred at room temperature overnight, and then diluted with toluene (10 mL). The mixture was concentrated in vacuo and the residue was washed with DCM twice. The DCM solution was collected and purified by flash chromatography to give the title compound as white solid (12 mg).

EXAMPLE 51

Preparation of intermediate (4-chloro-2-formyl-phenoxy)-acetic acid methyl ester

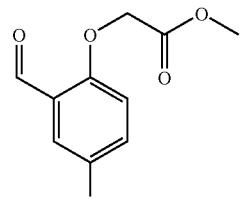

M.W. 228.63
$C_{10}H_9ClO_4$

A mixture of 5-chloro-2-hydroxy-benzaldehyde (35 g, 220 mmol), bromo-acetic acid methyl ester (43 g, 282 mmol), $K_2CO_3$ (60 g, 434 mmol) and in DMF (300 mL) was heated at 140° C. for 10 min. Then the mixture was partitioned between ethyl acetate and water. The organic layer was separated, washed with water 4 times, dried over anhydrous $Na_2SO_4$, concentrated to give crude product as yellow solid (50 g).

EXAMPLE 52

Preparation of intermediate E/Z-[4-chloro-2-(6-chloro-2-oxo-1,2-dihydro-indol-3-ylidenemethyl)-phenoxy]-acetic acid methyl ester

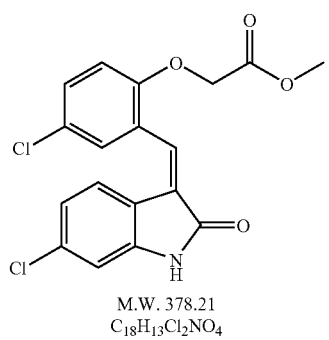

M.W. 378.21
$C_{18}H_{13}Cl_2NO_4$

To the mixture of 6-chloro-1,3-dihydro-indol-2-one (10 g, 60 mmol) and (4-chloro-2-formyl-phenoxy)-acetic acid methyl ester (15.2 g, 67 mmol) in methanol (100 mL) was added pyrrolidine (4.5 g, 63 mmol) dropwise. The mixture was then heated at 80° C. for 1 h. After cooled to room temperature, the mixture was filtered and resulting precipitate was collected, dried to give the title compound as a yellow solid (12 g).

EXAMPLE 53

Preparation of intermediate E/Z-6-chloro-3-(5-chloro-2-methoxycarbonylmethoxy-benzylidene)-2-oxo-2,3-dihydro-indole-1-carboxylic acid tert-butyl ester

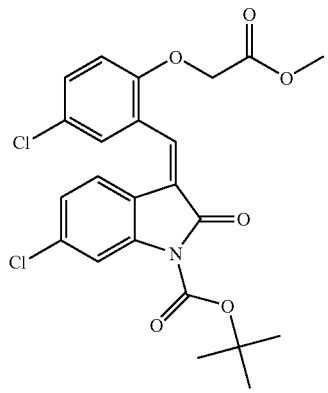

M.W. 478.33
$C_{23}H_{21}Cl_2NO_6$

At room temperature, to a solution E/Z-[4-chloro-2-(6-chloro-2-oxo-1,2-dihydro-indol-3-ylidenemethyl)-phenoxy]-acetic acid methyl ester (5.3 g, 14 mmol) in dichloromethane (100 mL) was added di-tert-butyl-dicarbonate (3.7 g, 16.9 mmol), followed by the addition of 4-dimethylaminopyridine (0.17 g, 1.4 mmol). The reaction mixture was stirred at room temperature for 1 h. Then the mixture was concentrated and the residue was purified by chromatography to give the title compound as an yellow solid (5.1 g).

EXAMPLE 54

Preparation of intermediate racemic (2'S, 3S, 4'R)-6-chloro-4'-[5-chloro-2-(2-methoxycarbonyl-methoxy)-phenyl]-2'-[5-difluoro-2-methyl-phenyl]spiro[3H-indole-3,3'-piperidine]-2,6'(1H)-dione

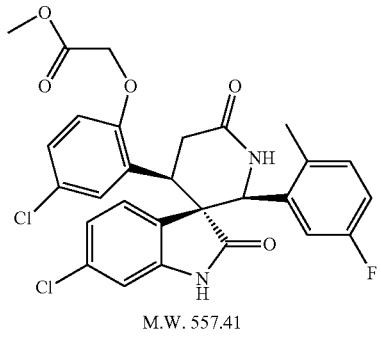

M.W. 557.41
$C_{28}H_{23}Cl_2FN_2O_5$

A mixture of E/Z-6-chloro-3-(5-chloro-2-methoxycarbonylmethoxy-benzylidene)-2-oxo-2,3-dihydro-indole-1-carboxylic acid tert-butyl ester (3 g, 6.2 mmol) and 1-(5-fluoro-2-methylphenyl)-3-trimethylsilyoxy-2-aza-1,3-butadiene (18 mmol) prepared in Example 4 in toluene (18 mL) was heated at 60° C. for 3 h, and concentrated in vacuo. To the residue was added DCM (30 mL) and TFA (10 mL), and the resultant solution was stirred at room temperature for 3 h, then concentrated in vacuo. The residue was partitioned between ethyl acetate and diluted aqueous NaOH solution. The organic layer was washed with water, dried over anhydrous $Na_2SO_4$, and concentrated. The residue was purified by flash chromatography to give the title compound as white solid (700 mg).

EXAMPLE 55

Preparation of racemic (2'S, 3S, 4'R)-6-chloro-4'-[5-chloro-2-(2-methoxycarbonyl-methoxy)-phenyl]-2'-[5-difluoro-2-methyl-phenyl]-6'-thioxo spiro[3H-indole-3,3'-piperidine]-2(1H)-one

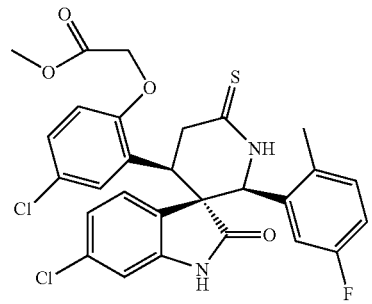

M.W. 573.47
C28H23Cl2FN2O4S

A mixture of racemic (2'S, 3S, 4'R)-6-chloro-4'-[5-chloro-2-(2-methoxycarbonyl-methoxy)-phenyl]-2'-[5-difluoro-2-methyl-phenyl]spiro[3H-indole-3,3'-piperidine]-2,6'(1H)-dione (40 mg, 0.07 mmol) and $P_2S_5$ (50 mg, 0.23 mmol) in THF (2 mL) was heated at 50° C. for 2 h, and then diluted with toluene (10 mL). The mixture was concentrated in vacuo and the residue was washed with DCM twice. The DCM solutions was combined and concentrated. The residue was purified by flash chromatography to give the title compound as white solid (25 mg).

EXAMPLE 56

Preparation of intermediate1-(4,5-difluoro-2-methyl-phenyl)-3-trimethylsilyoxy-2-aza-1,3-butadiene

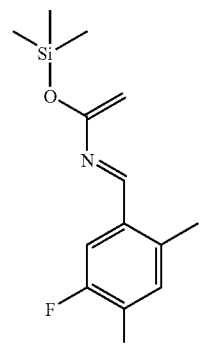

M.W. 269.37
$C_{13}H_{17}F_2NOSi$

To dry tetrahydrofuran (15 mL) was added 1M THF solution of LiHMDS (24.7 mmol, 24.7 mL) under Ar protection at room temperature, followed by the addition of 2-methyl-4,5-difluoro-benzaldehyde (3.86 g, 24.7 mmol). After the mixture was stirred at room temperature for 1 h, trimethylsilyl chloride (3.1 mL, 24.7 mmol) was added dropwise. Then the temperature of the mixture was lowered to 0° C. on a cooling ice bath. To this mixture was added triethylamine (4.47 mL, 32 mmol) in one portion, followed by the dropwise addition of a solution of acetyl chloride (2.35 mL, 32 mmol) in diethyl ether (50 mL). The cooling bath was removed, and the mixture was stirred at room temperature for 4 h. The mixture was quickly filtered on celite under nitrogen, and filtrate was concentrated under reduced pressure to give crude 1-(4,5-difluoro-2-methyl-phenyl)-3-trimethylsilyoxy-2-aza-1,3-butadiene as a yellow gum and used for the next step without further purification.

EXAMPLE 57

Preparation of intermediate racemic (2'S, 3S, 4'R)-6-chloro-4'-[5-chloro-2-(1-methoxycarbonyl-1-methyl-ethoxy)-phenyl]-2'-(4,5-difluoro-2-methyl-phenyl) spiro[3H-indole-3,3'-piperidine]-2,6'(1H)-dione

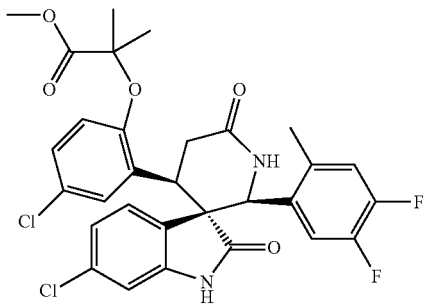

M.W. 603.45
C30H26Cl2F2N2O5

A mixture of E/Z-6-chloro-3-[5-chloro-2-(1-methoxycarbonyl-1-methyl-ethoxy)-benzylidene]-2-oxo-2,3-dihydro-indole-1-carboxylic acid tert-butyl ester (1.5 g, 2.9 mmol) and 1-(4,5-difluoro-2-methyl-phenyl)-3-trimethylsilyoxy-2-aza-1,3-butadiene (13 mmol) in toluene (13 mL) was heated at 60° C. for 3 h, and concentrated in vacuo. To the residue was added DCM (30 mL) and TFA (5 mL), and the resultant solution was stirred at room temperature for 3 h, then concentrated in vacuo. The residue was partitioned between ethyl acetate and aqueous diluted NaOH solution. The organic layer was washed with water to neutral, dried over anhydrous Na2SO4, and concentrated. The residue was purified by flash chromatography to give the title compound as white solid (60 mg).
m/z (M+H)+: 603

EXAMPLE 58

Preparation of racemic (2'S, 3S, 4'R)-6-chloro-4'-[5-chloro-2-(1-methoxycarbonyl-1-methyl-ethoxy)-phenyl]-2'-(4,5-difluoro-2-methyl-phenyl)-6'-thioxo spiro[3H-indole-3,3'-piperidine]-2(1H)-one

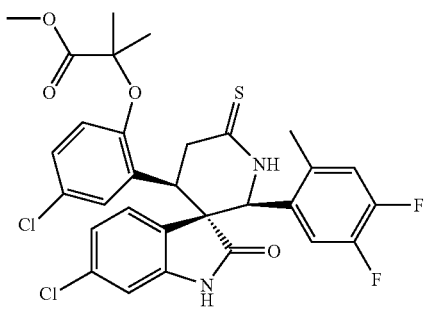

M.W. 619.52
C30H26Cl2F2N2O4S

A mixture of racemic (2'S, 3S, 4'R)-6-chloro-4'-[5-chloro-2-(1-methoxycarbonyl-1-methyl-ethoxy)-phenyl]-2'-(4,5-difluoro-2-methyl-phenyl) spiro[3H-indole-3,3'-piperidine]-2,6'(1H)-dione (40 mg, 0.067 mmol) and P2S5 (45 mg, 0.20 mmol) in THF (2 mL) was heated at 50° C. for 2 h, and then diluted with toluene (10 mL). The mixture was concentrated in vacuo and the residue was washed with DCM twice. The DCM extracts were combined and concentrated. The residue was purified by flash chromatography to give the title compound as white solid (10 mg).

EXAMPLE 59

Preparation of intermediate E/Z-6-chloro-3-(5-chloro-4-fluoro-2-methoxy-benzylidene)-1,3-dihydro-indol-2-one

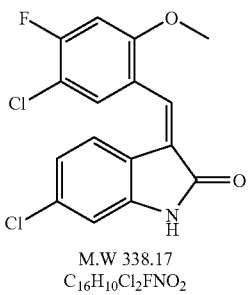

M.W 338.17
C16H10Cl2FNO2

To the mixture of 6-chloro-1,3-dihydro-indol-2-one (3.4 g, 20.3 mmol) and 5-chloro-4-fluoro-2-methoxy-benzaldehyde (3.2 g, 17 mmol) in methanol (50 mL) was added pyrrolidine (1.2 g, 17 mmol) dropwise. Then the mixture was heated at 70° C. for 1 h. After cooled to room temperature, the mixture was filtered to give the crude product which was used for the next step reaction without further purification.

EXAMPLE 60

Preparation of intermediate E/Z-6-chloro-3-(5-chloro-4-fluoro-2-methoxy-benzylidene)-2-oxo-2,3-dihydro-indole-1-carboxylic acid tert-butyl ester

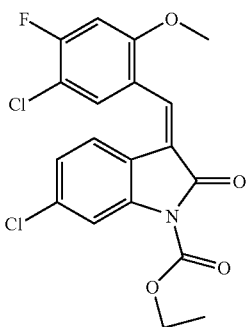

M.W. 438.29
C21H18Cl2FNO4

To a solution of E/Z-6-chloro-3-(5-chloro-4-fluoro-2-methoxy-benzylidene)-1,3-dihydro-indol-2-one (4.5 g, 13.3 mmol) in dichloromethane (50 mL) at room temperature was added di-tert-butyl-dicarbonate (3.5 g, 16 mmol), followed by the addition of 4-dimethylaminopyridine (1 g, 8.2 mmol). After stirred at room temperature for 2 h, the solution was concentrated and the residue was purified by flash chromatography to give the title compound as a orange solid (4 g).

EXAMPLE 61

Preparation of intermediate racemic (2'R, 3R, 4'S)-6-chloro-4'-[5-chloro-4-fluoro-2-methoxy-phenyl]-2'-(5-fluoro-2-methyl-phenyl) spiro[3H-indole-3,3'-piperidine]-2,6'(1H)-dione

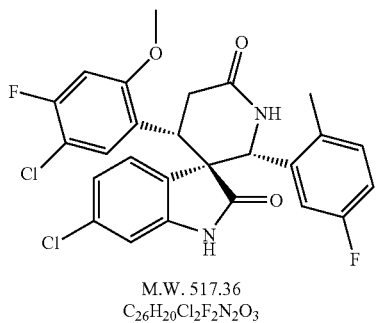

M.W. 517.36
$C_{26}H_{20}Cl_2F_2N_2O_3$

A mixture of E/Z-6-chloro-3-(5-chloro-4-fluoro-2-methoxy-benzylidene)-2-oxo-2,3-dihydro-indole-1-carboxylic acid tert-butyl ester (3 g, 6.8 mmol) and 1-(5-fluoro-2-methyl-phenyl)-3-trimethylsilyoxy-2-aza-1,3-butadiene (30 mmol) prepared in Example 4 in toluene (30 mL) was heated at 60° C. for 3 h, and concentrated in vacuo. To the residue was added DCM (30 mL) and TFA (5 mL), and the resultant solution was stirred at room temperature for 3 h, then concentrated. The residue was partitioned between ethyl acetate and aqueous diluted NaOH solution. The organic layer was washed with water, dried over anhydrous $Na_2SO_4$, and concentrated. The residue was purified by flash chromatography to give the title compound as white solid (60 mg).

EXAMPLE 62

Preparation of racemic (2'R, 3R, 4'S)-6-chloro-4'-[5-chloro-4-fluoro-2-methoxy-phenyl]-2'45-fluoro-2-methyl-phenyl)-6'-thioxo spiro[3H-indole-3,3'-piperidine]-2(1H)-one

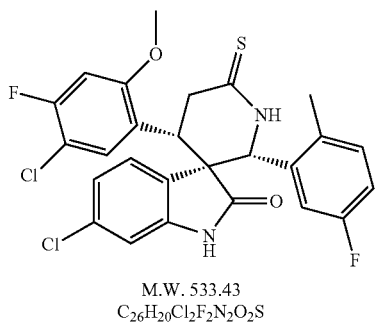

M.W. 533.43
$C_{26}H_{20}Cl_2F_2N_2O_2S$

A mixture of racemic (2'R, 3R, 4'S)-6-chloro-4'-[5-chloro-4-fluoro-2-methoxy-phenyl]-2'-(5-fluoro-2-methyl-phenyl) spiro[3H-indole-3,3'-piperidine]-2,6'(1H)-dione (40 mg, 0.077 mmol) and $P_2S_5$ (52 mg, 0.23 mmol) in THF (2 mL) was heated at 50° C. for 2 h, and then diluted with toluene (10 mL). The mixture was concentrated and the residue was washed with DCM twice. The DCM layers were combined and concentrated. The residue was purified by flash chromatography to give the title compound as white solid (30 mg).

EXAMPLE 63

Preparation of intermediate 1-(5,6-difluoro-2-methyl-phenyl)-3-trimethylsilyoxy-2-aza-1,3-butadiene

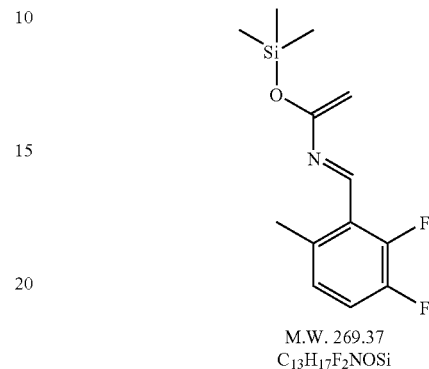

M.W. 269.37
$C_{13}H_{17}F_2NOSi$

To dry tetrahydrofuran (15 mL) was added 1M THF solution of LiHMDS (24.7 mmol, 24.7 mL) under Ar protection at room temperature, followed by the addition of 5,6-difluoro-2-methyl-benzaldehyde (3.86 g, 24.7 mmol). After the mixture was stirred at room temperature for 1 h, trimethylsilyl chloride (3.1 mL, 24.7 mmol) was added dropwise. Then the temperature of the mixture was lowered to 0° C. on a cooling ice bath. To this mixture was added triethylamine (4.47 mL, 32 mmol) in one portion, followed by the dropwise addition of a solution of acetyl chloride (2.35 mL, 32 mmol) in diethyl ether (30 mL). The cooling bath was removed, and the mixture was stirred at room temperature for 4 h. The mixture was quickly filtered on celite under nitrogen, and filtrate was concentrated under reduced pressure to give crude 1-(5,6-difluoro-2-methyl-phenyl)-3-trimethylsilyoxy-2-aza-1,3-butadiene as a yellow gum and used for the next step without further purification.

EXAMPLE 64

Preparation of intermediate racemic (2'S, 3S, 4'R)-6-chloro-4'-[5-chloro-2-(1-methoxycarbonyl-1-methyl-ethoxy)-phenyl]-2'-(5,6-difluoro-2-methyl-phenyl) spiro[3H-indole-3,3'-piperidine]-2,6'(1H)-dione

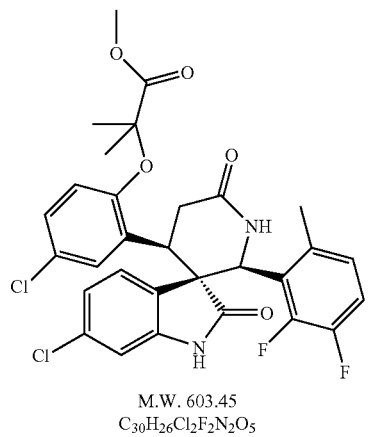

M.W. 603.45
$C_{30}H_{26}Cl_2F_2N_2O_5$

A mixture of racemic (2'S, 3S, 4'R)-6-chloro-4'-[5-chloro-2-(1-methoxycarbonyl-1-methyl-ethoxy)-phenyl]-2'-(5,6-difluoro-2-methyl-phenyl) spiro[3H-indole-3,3'-piperidine]-2,6'(1H)-dione (3 g, 5.94 mmol) prepared in Example 3 and 1-(5,6-difluoro-2-methyl-phenyl)-3-trimethylsilyoxy-2-aza-1,3-butadiene (18 mmol) in toluene (18 mL) was heated at 60° C. for 3 h, and concentrated. To the residue was added DCM (30 mL) and TFA (10 mL), and the resultant solution was stirred at room temperature for 3 h, then concentrated in vacuo. The residue was partitioned between ethyl acetate and diluted aqueous NaOH solution. The organic layer was separated, washed with water, dried over anhydrous $Na_2SO_4$, and concentrated. The residue was purified by flash chromatography to give the title compound as white solid (180 mg).
m/z (M+H)$^+$: 603

EXAMPLE 65

Preparation of racemic (2'S, 3S, 4'R)-6-chloro-4'-[5-chloro-2-(1-methoxycarbonyl-1-methyl-ethoxy)-phenyl]-2'-(5,6-difluoro-2-methyl-phenyl)-6'-thioxo spiro[3H-indole-3,3'-piperidine]-2(1H)-one

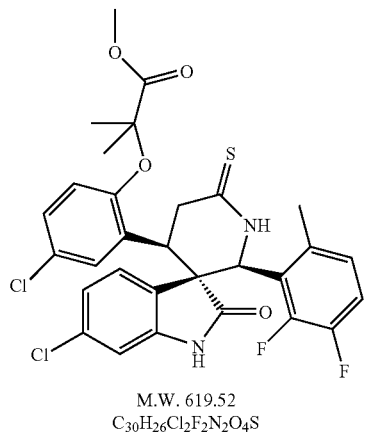

M.W. 619.52
$C_{30}H_{26}Cl_2F_2N_2O_4S$

A mixture of racemic (2'S, 3S, 4'R)-6-chloro-4'-[5-chloro-2-(1-methoxycarbonyl-1-methyl-ethoxy)-phenyl]-2'-(5,6-difluoro-2-methyl-phenyl) spiro[3H-indole-3,3'-piperidine]-2,6'(1H)-dione (40 mg, 0.067 mmol) and $P_2S_5$ (45 mg, 0.20 mmol) in THF (2 mL) was heated at 50° C. for 2 h, and then diluted with toluene (10 mL). The mixture was concentrated in vacuo and the residue was washed with DCM twice. The DCM layers were combined and concentrated. The residue was purified by flash chromatography to give the title compound as white solid (38 mg).

EXAMPLE 66

Preparation of intermediate 2-(4-chloro-5-fluoro-2-formyl-phenoxy)-2-methyl-propionic acid methyl ester

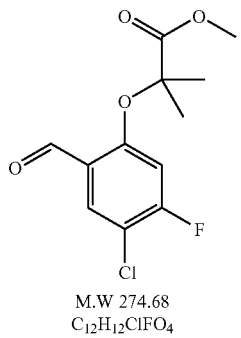

M.W 274.68
$C_{12}H_{12}ClFO_4$

A mixture of 5-chloro-4-fluoro-2-hydroxy-benzaldehyde (0.8 g, 4.6 mmol), 2-bromo-2-methyl-propionic acid methyl ester (1.6 g, 9.2 mmol) and $K_2CO_3$ (2 g, 14.5 mmol) in DMF (40 mL) was placed in a sealed tube and heated by irradiation in microwave reactor at 140° C. for 12 min. After cooled to room temperature, the mixture was partitioned between EtOAc and water. The organic layer was separated, washed with water, dried over anhydrous $Na_2SO_4$ and concentrated to give the thitle compound as a brown solid (1.08 g).

EXAMPLE 67

Preparation of intermediate E/Z-2-[4-chloro-2-(6-chloro-2-oxo-1,2-dihydro-indol-3-ylidenemethyl)-5-fluoro-phenoxy]-2-methyl-propionic acid methyl ester

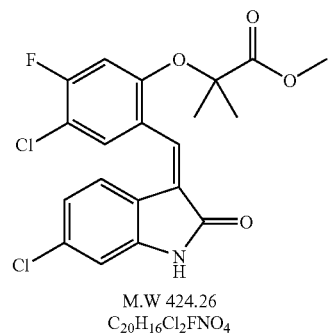

M.W 424.26
$C_{20}H_{16}Cl_2FNO_4$

To the mixture of 6-chloro-1,3-dihydro-indol-2-one (0.73 g, 4.4 mmol) and 2-(4-Chloro-5-fluoro-2-formyl-phenoxy)-2-methyl-propionic acid methyl ester (1 g, 3.65 mmol) in methanol (15 mL) was added pyrrolidine (0.26 g, 4.4 mmol) dropwise. Then the mixture was heated at 70° C. for 1 h. After cooled to room temperature, the mixture was concentrated to give the crude product which was used for the next step reaction without further purification.

EXAMPLE 68

Preparation of intermediate E/Z-6-chloro-3-[5-chloro-4-fluoro-2-(1-methoxycarbonyl-1-methyl-ethoxy)-benzylidene]-2-oxo-2,3-dihydro-indole-1-carboxylic acid tert-butyl ester

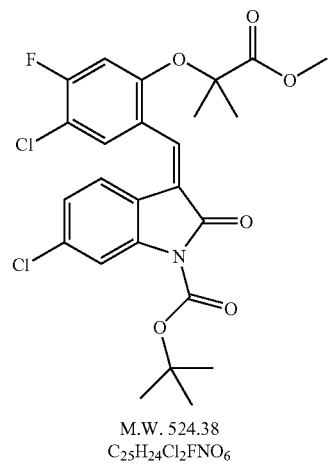

M.W. 524.38
$C_{25}H_{24}Cl_2FNO_6$

To a solution of E/Z-2-[4-chloro-2-(6-chloro-2-oxo-1,2-dihydro-indol-3-ylidenemethyl)-5-fluoro-phenoxy]-2-methyl-propionic acid methyl ester (1.5 g, 3.65 mmol) in dichloromethane (20 mL) at room temperature was added di-tert-butyl-dicarbonate (2.4 g, 11 mmol), followed by the addition of 4-dimethylaminopyridine (0.15 g, 1.2 mmol). After the reaction mixture was stirred at room temperature for 2 h, the solution was concentrated and the residue was purified by flash chromatography to give the title compound as a orange solid (1.4 g).

EXAMPLE 69

Preparation of intermediate racemic (2'S, 3S, 4'R)-6-chloro-4'-[5-chloro-4-fluoro-2-(1-methoxycarbonyl-1-methyl-ethoxy)-phenyl]-2'-(5-fluoro-2-methyl-phenyl) spiro[3H-indole-3,3'-piperidine]-2,6'(1H)-dione

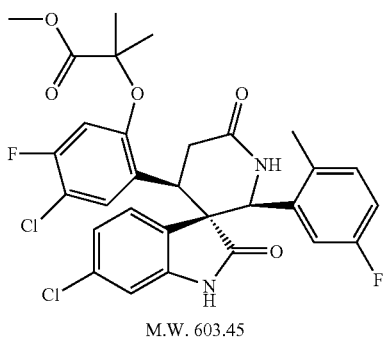

M.W. 603.45
$C_{30}H_{26}Cl_2F_2N_2O_5$

A mixture of, E/Z-6-chloro-3-[5-chloro-4-fluoro-2-(1-methoxycarbonyl-1-methyl-ethoxy)-benzylidene]-2-oxo-2,3-dihydro-indole-1-carboxylic acid tert-butyl ester (1.4 g, 2.6 mmol) and 1-(5-fluoro-2-methyl-phenyl)-3-trimethylsilyoxy-2-aza-1,3-butadiene (13 mmol) prepared in Example 4 in toluene (13 mL) was heated at 60° C. for 3 h, and concentrated. To the residue was added DCM (30 mL) and TFA (5 mL), and the resultant solution was stirred at room temperature for 3 h, then concentrated. The residue was partitioned between ethyl acetate and diluted aqueous NaOH solution. The organic layer was separated, washed with water, dried over anhydrous $Na_2SO_4$, and concentrated. The residue was purified by flash chromatography to give the title compound as white solid (60 mg).

EXAMPLE 70

Preparation of racemic (2'S, 3S, 4'R)-6-chloro-4'-[5-chloro-4-fluoro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one

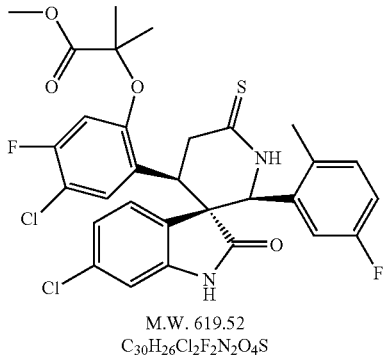

M.W. 619.52
$C_{30}H_{26}Cl_2F_2N_2O_4S$

A mixture of racemic (2'S, 3S, 4'R)-6-chloro-4'-[5-chloro-4-fluoro-2-(1-methoxycarbonyl-1-methyl-ethoxy)-phenyl]-2'-(5-fluoro-2-methyl-phenyl) spiro[3H-indole-3,3'-piperidine]-2,6'(1H)-dione (40 mg, 0.067 mmol) and $P_2S_5$ (45 mg, 0.20 mmol) in THF (2 mL) was heated at 50° C. for 2 h, and then diluted with toluene (10 mL). The mixture was concentrated and the residue was washed with DCM twice. The DCM solutions were combined and concentrated. The residue was purified by flash column to give the title compound as white solid (26 mg).

EXAMPLE 71

Preparation of intermediate racemic (2'S, 3S, 4'R)-6-chloro-4'-[5-chloro-2-(1-hydroxycarbonyl-1-methyl-ethoxy)-phenyl]-2'-(5-fluoro-2-methyl-phenyl) spiro [3H-indole-3,3'-piperidine]-2,6'(1H)-dione

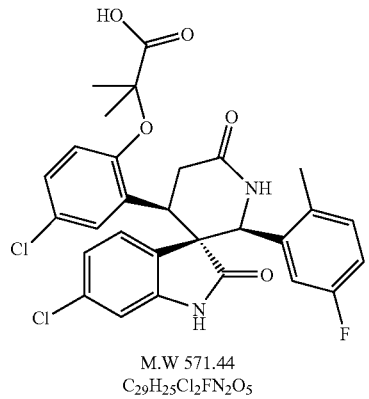

M.W 571.44
$C_{29}H_{25}Cl_2FN_2O_5$

Racemic (2'S, 3S, 4'R)-6-chloro-4'-[5-chloro-2-(1-ethoxycarbonyl-1-methyl-ethoxy)-phenyl]-2'-(5-fluoro-2-methyl phenyl) spiro[3H-indole-3,3'-piperidine]-2,6'(1H)-dione (2.7 g, 4.5 mmol) prepared in Example 5 was dissolved in THF (20 mL). Then aqueous solution (10 mL) of KOH (0.5 g) was added. The mixture was refluxed for 1 h. After cooled to room temperature, the solution was concentrated and then the residue was acidified to "pH" 2-3 by addition of concentrated aqueous HCl solution. The white solid was collected by filtration to give title compound (1.6 g).
m/z (M+H)$^+$: 571

EXAMPLE 72

Preparation of intermediate racemic (2'S, 3S, 4'R)-6-chloro-4'-[5-chloro-2-(1-methoxycarbamoyl-1-methyl-ethoxy)-phenyl]-2'-(5-fluoro-2-methyl-phenyl) spiro[3H-indole-3,3'-piperidine]-2,6'(1H)-dione

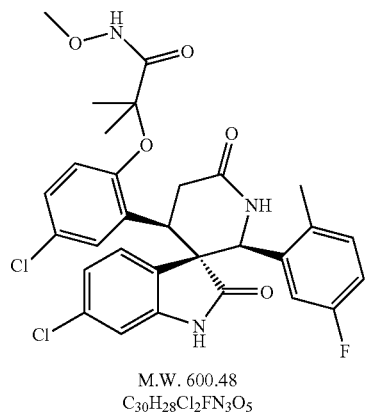

M.W. 600.48
$C_{30}H_{28}Cl_2FN_3O_5$

To a mixture of racemic (2'S, 3S, 4'R)-6-chloro-4'-[5-chloro-2-(1-hydroxycarbonyl-1-methyl-ethoxy)-phenyl]-2'-(5-fluoro-2-methyl-phenyl) spiro[3H-indole-3,3'-piperidine]-2,6'(1H)-dione (30 mg, 0.05 mmol), EDCI (20 mg, 0.1 mmol), HOBt (16 mg, 0.1 mmol) and DIPEA (40 mg, 0.3 mmol) in THF (1 mL) was added o-methylhydroxylamine hydrochloride (22 mg, 0.25 mmol). The mixture was stirred at room temperature overnight and purified by prep-HPLC to give the title compound as a white solid (11 mg).

m/z (M+H)⁺: 600

EXAMPLE 73

Preparation of racemic (2'S, 3S, 4'R)-6-chloro-4'-[5-chloro-2-(1-methoxycarbamoyl-1-methyl-ethoxy)-phenyl]-2'-(5-fluoro-2-methyl-phenyl)-6'-thioxo spiro[3H-indole-3,3'-piperidine]-2(1H)-one

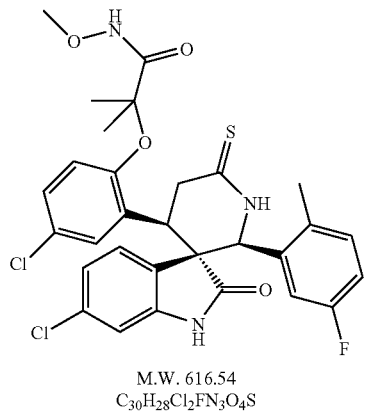

M.W. 616.54
$C_{30}H_{28}Cl_2FN_3O_4S$

A mixture of racemic (2'S, 3S, 4'R)-6-chloro-4'-[5-chloro-2-(1-methoxycarbamoyl-1-methyl-ethoxy)-phenyl]-2'-(5-fluoro-2-methyl-phenyl) spiro[3H-indole-3,3'-piperidine]-2,6'(1H)-dione (25 mg, 0.042 mmol) and Lawesson's reagent (33 mg, 0.084 mmol) in THF (1 mL) was stirred at room temperature for 1 h, and then diluted with toluene (10 mL). The mixture was concentrated and the residue was washed with DCM twice. The DCM solutions were combined and concentrated. The residue was purified by flash column to give the title compound as white solid (10 mg).

EXAMPLE 74

Preparation of intermediate racemic (2'S, 3S, 4'R)-6-chloro-4'-[5-chloro-2-(1-methoxycarbamoyl-1-ethyl-propoxy)-phenyl]-2'-(5-fluoro-2-methyl-phenyl) spiro[3H-indole-3,3'-piperidine]-2,6'(1H)-dione

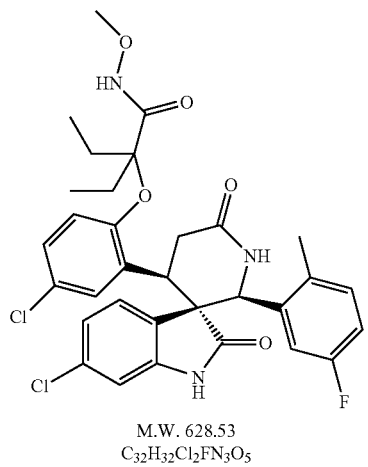

M.W. 628.53
$C_{32}H_{32}Cl_2FN_3O_5$

To a mixture of racemic (2'S, 3S, 4'R)-6-chloro-4'-[5-chloro-2-(1-hydroxycarbonyl-1-ethyl-propoxy)-phenyl]-2'-(5-fluoro-2-methyl-phenyl) spiro[3H-indole-3,3'-piperidine]-2,6'(1H)-dione (50 mg, 0.084 mmol) prepared in Example 18, HATU (65 mg, 0.17 mmol) and DIPEA (66 mg, 0.54 mmol) in THF (1 mL) was added o-methylhydroxylamine hydrochloride (22 mg, 0.25 mmol). The mixture was stirred at room temperature overnight and purified by prep-HPLC to give the title compound as a white solid (12 mg).

EXAMPLE 75

Preparation of racemic (2'S, 3S, 4'R)-6-chloro-4'-[5-chloro-2-(1-methoxycarbamoyl-1-ethyl-propoxy)-phenyl]-2'-(5-fluoro-2-methyl-phenyl)-6'-thioxo spiro[3H-indole-3,3'-piperidine]-2(1)-one

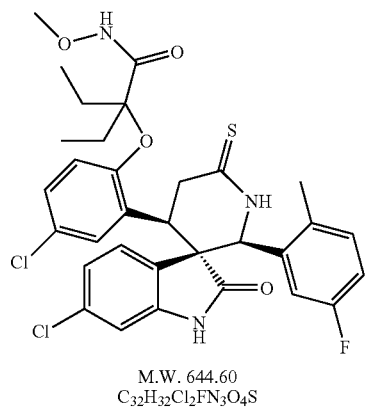

M.W. 644.60
$C_{32}H_{32}Cl_2FN_3O_4S$

A mixture of racemic (2'S, 3S, 4'R)-6-chloro-4'-[5-chloro-2-(1-methoxycarbamoyl-1-ethyl-propoxy)-phenyl]-2'-(5-fluoro-2-methyl-phenyl) spiro[3H-indole-3,3'-piperidine]-2,6'(1H)-dione (12 mg, 0.02 mmol) and $P_2S_5$ (18 mg, 0.08 mmol) in THF (0.5 mL) was heated at 60° C. for 2 h, and then diluted with toluene (10 mL). The mixture was concentrated and the residue was washed with DCM twice. The DCM solutions were combined and concentrated. The residue was purified by prep-TLC to give the title compound as white solid (10 mg).

EXAMPLE 76

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co. $IC_{50}$'s showing the biological activity of this invention exhibit activities less than about 10 uM.

Representative values are, for example:

| Example | $IC_{50}$ (μM, 0.02% BSA) |
| --- | --- |
| 8 | 0.05 |
| 24 | 0.022 |
| 50 | 4.331 |
| 62 | 1.093 |
| 73 | 0.607 |

What is claimed:
1. A compound of the formula

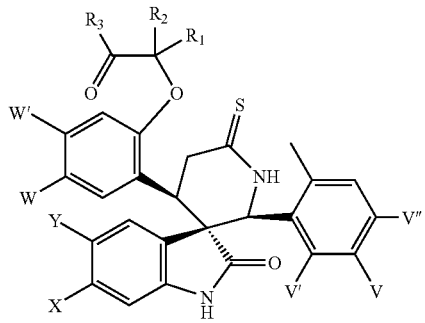

I wherein
X is Cl,
Y is hydrogen,
V is F or Cl,
V' is hydrogen or F,
V" is hydrogen,
W is Cl,
W' is hydrogen,
$R_1$ and $R_2$ are methyl or ethyl,
or $R_1$ and $R_2$ may link to form a cyclic structure selected from a substituted or unsubstituted cycloalkyl
$R_3$ is NHS($=$O)$_2$R",
R', R" is selected independently from the group consisting of lower alkyl, substituted alkyl, cycloalkyl and substituted cycloalkyl
and the pharmaceutically acceptable salts and esters and enantiomers thereof.

2. A compound selected from the group consisting of
chiral (2'S, 3S, 4'R)-6-chloro-4'-[5-chloro-2-(1-hydroxycarbonyl-1-methyl-ethoxy)-phenyl]-2'-(5-fluoro-2-methyl-phenyl)-6'-thioxo spiro[3H-indole-3,3'-piperidine]-2(1H)-one,
racemic (2'S, 3S, 4'R)-6-chloro-4'-[5-chloro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one,
chiral (2'S, 3S, 4'R)-6-chloro-4'-[5-chloro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one,
chiral (2'S, 3S, 4'R)-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one,
chiral (2'R, 3R, 4'S)-6-chloro-4'-[5-chloro-2-(2-methanesulfonylamino-1,1-diethyl-2-oxo-ethoxy)-phenyl]-2'-(5-fluoro-2-methyl-phenyl)-6'-thioxo spiro[3H-indole-3,3'-piperidine]-2(1H)-one,
chiral (2'S, 3S, 4'R)-6-chloro-4'-[5-chloro-2-(2-methanesulfonylamino-1,1-diethyl-2-oxo-ethoxy)-phenyl]-2'-(5-chloro-2-methyl-phenyl)-6'-thioxo spiro[3H-indole-3,3'-piperidine]-2(1H)-one,
racemic (2'S, 3S, 4'R)-6-chloro-4'-[5-chloro2-(1-ethoxycarbonyl-1-propyl-butoxy)-phenyl]-2'-(5-fluoro-2-methyl-phenyl)-6'-thioxo spiro[3H-indole-3,3'-piperidine]-2(1H)-one,
chiral (2'S, 3S, 4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-6'-thioxo spiro[3H-indole-3,3'-piperidine]-2(1H)-one and
racemic (2'S, 3S, 4'R)-6-chloro-4'-[5-chloro-2-(1-methoxycarbonyl-cyclobutoxy)-phenyl]-2'-(5-fluoro-2-methyl-phenyl)-6'-thioxo spiro[3H-indole-3,3'-piperidine]-2(1H)-one.

3. A compound selected from the group consisting of
racemic (2'S, 3S, 4'R)-6-chloro-4'-[5-chloro-2-(2-methoxycarbonyl-methoxy)-phenyl]-2'-[5-difluoro-2-methyl-phenyl]-6'-thioxo spiro[3H-indole-3,3'-piperidine]-2(1 H)-one,
racemic (2'S, 3S, 4'R)-6-chloro-4'-[5-chloro-2-(1-methoxycarbonyl-1-methyl-ethoxy)-phenyl]-2'-(4,5-difluoro-2-methyl-phenyl)-6'-thioxo spiro[3H-indole-3,3'-piperidine]-2(1H)-one,
racemic (2'R, 3R, 4'S)-6-chloro-4'-[5-chloro-4-fluoro-2-methoxy-phenyl]-2'-(5-fluoro-2-methyl-phenyl)-6'-thioxo spiro[3H-indole-3,3'-piperidine]-2(1 H)-one,
racemic (2'S, 3S, 4'R)-6-chloro-4'-[5-chloro-2-(1-methoxycarbonyl-1-methyl-ethoxy)-phenyl]-2'-(5,6-difluoro-2-methyl-phenyl)-6'-thioxo spiro[3H-indole-3,3'-piperidine]-2(1H)-one,
racemic (2'S, 3S, 4'R)-6-chloro-4'-[5-chloro-4-fluoro-2-(1-methoxycarbonyl-1-methyl-ethoxy)-phenyl]-2'-(5-fluoro-2-methyl-phenyl)-6'-thioxo spiro[3H-indole-3,3'-piperidine]-2(1H)-one,
racemic (2'S, 3S, 4'R)-6-chloro-4'-[5-chloro-2-(1-methoxylcarbamoyl-1-methyl-ethoxy)-phenyl]-2'-(5-fluoro-2-methyl-phenyl)-6'-thioxo spiro[3H-indole-3,3'-piperidine]-2(1H)-one and
racemic (2'S, 3S, 4'R)-6-chloro-4'-[5-chloro-2-(1-methoxylcarbamoyl-1-ethyl-propoxy)-phenyl]-2'-(5-fluoro-2-methyl-phenyl)-6'-thioxo spiro[3H-indole-3,3'-piperidine]-2(1H)-one.

4. A pharmaceutical composition comprising a compound of the formula

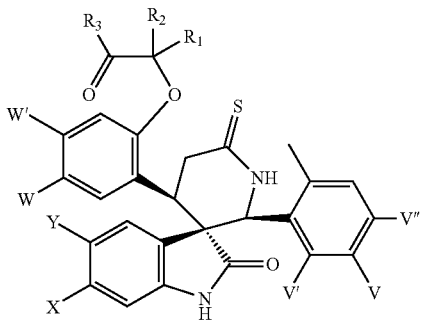

wherein
X is Cl,
Y is hydrogen,
V is F or Cl,
V' is hydrogen,
V" is hydrogen or F,
W is Cl,
W' is hydrogen,
$R_1$ and $R_2$ are methyl or ethyl,
$R_3$ is $NHS(=O)_2R"$,
R', R" is selected independently from the group consisting of lower alkyl, substituted alkyl, cycloalkyl and substituted cycloalkyl
and the pharmaceutically acceptable salts and esters and enantiomers thereof together with a pharmaceutically acceptable excipient or carrier.

* * * * *